United States Patent
Rae et al.

(10) Patent No.: US 12,296,085 B2
(45) Date of Patent: May 13, 2025

(54) METHOD FOR EXTRACORPOREAL TREATMENT OF PREECLAMPSIA AND RELATED DISORDERS

(71) Applicant: Immutrix Therapeutics, Inc., Rapid City, SD (US)

(72) Inventors: Carol A. Rae, Rapid City, SD (US); Jan Simoni, Rapid City, SD (US); John F. Moeller, Rapid City, SD (US)

(73) Assignee: Immutrix Therapeutics, Inc., Rapid City, SD (US)

( * ) Notice: Subject to any disclaimer, the term of this patent is extended or adjusted under 35 U.S.C. 154(b) by 0 days.

(21) Appl. No.: 16/088,785

(22) PCT Filed: Mar. 31, 2017

(86) PCT No.: PCT/US2017/025362
§ 371 (c)(1),
(2) Date: Sep. 26, 2018

(87) PCT Pub. No.: WO2017/173260
PCT Pub. Date: Oct. 5, 2017

(65) Prior Publication Data
US 2019/0105631 A1   Apr. 11, 2019

Related U.S. Application Data

(60) Provisional application No. 62/316,113, filed on Mar. 31, 2016.

(51) Int. Cl.
| | |
|---|---|
| *A61M 1/36* | (2006.01) |
| *A61K 33/44* | (2006.01) |
| *A61M 1/34* | (2006.01) |
| *B01D 15/00* | (2006.01) |
| *B01J 20/20* | (2006.01) |
| *B01J 20/26* | (2006.01) |
| *B01J 20/28* | (2006.01) |
| *B01J 20/32* | (2006.01) |

(52) U.S. Cl.
CPC ........... *A61M 1/3679* (2013.01); *A61K 33/44* (2013.01); *A61M 1/3486* (2014.02); *B01D 15/00* (2013.01); *B01J 20/20* (2013.01); *B01J 20/265* (2013.01); *B01J 20/28016* (2013.01); *B01J 20/28052* (2013.01); *B01J 20/28092* (2013.01); *B01J 20/3204* (2013.01); *B01J 20/321* (2013.01); *B01J 20/3212* (2013.01); *B01J 20/3242* (2013.01); *B01J 20/3293* (2013.01)

(58) Field of Classification Search
None
See application file for complete search history.

(56) References Cited

U.S. PATENT DOCUMENTS

| | | | | |
|---|---|---|---|---|
| 8,349,325 | B2 * | 1/2013 | Brophy | A61P 9/12 424/133.1 |
| 2007/0098804 | A1 * | 5/2007 | Aronhime | A61K 9/1688 424/489 |
| 2007/0104707 | A1 * | 5/2007 | Karumanchi | A61K 31/4439 424/133.1 |
| 2011/0160636 | A1 * | 6/2011 | Bansal | C07K 16/18 604/6.09 |
| 2012/0156201 | A1 * | 6/2012 | Naparstek | A61P 3/10 424/133.1 |
| 2013/0072845 | A1 * | 3/2013 | Tennison | A61M 1/3486 604/5.04 |
| 2015/0320924 | A1 * | 11/2015 | Flieg | B01D 61/00 210/638 |

FOREIGN PATENT DOCUMENTS

| | | | | |
|---|---|---|---|---|
| CA | 2522802 | * | 10/2004 | G01N 33/547 |
| WO | WO 2005/099789 | * | 10/2005 | A61M 1/34 |
| WO | WO2008157570 | * | 12/2008 | A61M 1/34 |
| WO | WO 2010/062678 | * | 6/2010 | A61K 9/14 |
| WO | WO 2011/112873 | * | 9/2011 | A61K 39/395 |
| WO | WO 2015/161200 | * | 10/2015 | A61K 47/02 |
| WO | WO 2016/164567 | * | 10/2016 | C07K 16/28 |

OTHER PUBLICATIONS

Liu et al., Cancer Medicine 2014; 3(3): 580-591 (Year: 2014).*
Barnett et al., Invest Ophthalmol Vis Sci. 2014; 55: 6490-6498 (Year: 2014).*
Wang and Yu, Artificial Cells, Blood Substitutes, and Biotechnology, 2011; 39: 92-97 (Year: 2011).*
Arora et al., Curr Protein Pept Sci. 2017; 18(9) :946-955. doi: 10.2174/1389203717666160724202806. (Year: 2017).*
Page 200 of T.K. Goswami and S. Mangaraj, In: Advances in polymeric materials for modified atmosphere packaging (MAP), Editor (s): José-María Lagarón, Multifunctional and Nanoreinforced Polymers for Food Packaging, Woodhead Publishing, 2011, pp. 163-242, ISBN 9781845697389 (Year: 2011).*
Mora-Palazuelos et al., Medicine 2022;101:39(e30870) (Year: 2022).*
Dimitriades et al., Nature Reviews Disease Primers (2023) 9:8 (Year: 2023).*
Gleicher et al., Am J Obstet Gynecol 2007;196:5.e1-5.e7 (Year: 2007).*

* cited by examiner

*Primary Examiner* — Christina M Borgeest
(74) *Attorney, Agent, or Firm* — Barnes & Thornburg LLP; Jerry C. Harris, Jr.

(57) ABSTRACT

A three-component composition for use in the treatment of preeclampsia and related disorders wherein a first component comprises a bimodal synthetic carbon particle mixture; a second component comprises a resin bead with at least one affinity ligand directed toward syncytiotrophoblast-derived factor sEndoglin and a third component comprises a resin bead with at least one affinity ligand directed toward syncytiotrophoblast-derived factor soluble Fms-like tyrosine kinase-1.

8 Claims, 9 Drawing Sheets

Anti-sFlt-1 Ab and Anti-sEndoglin Ab Covalently Attached To
Modified Polyvinyl Alcohol Beads (PVA)

SBCP With Sorbing Potency Towards Molecules Relevant
in Preeclampsia

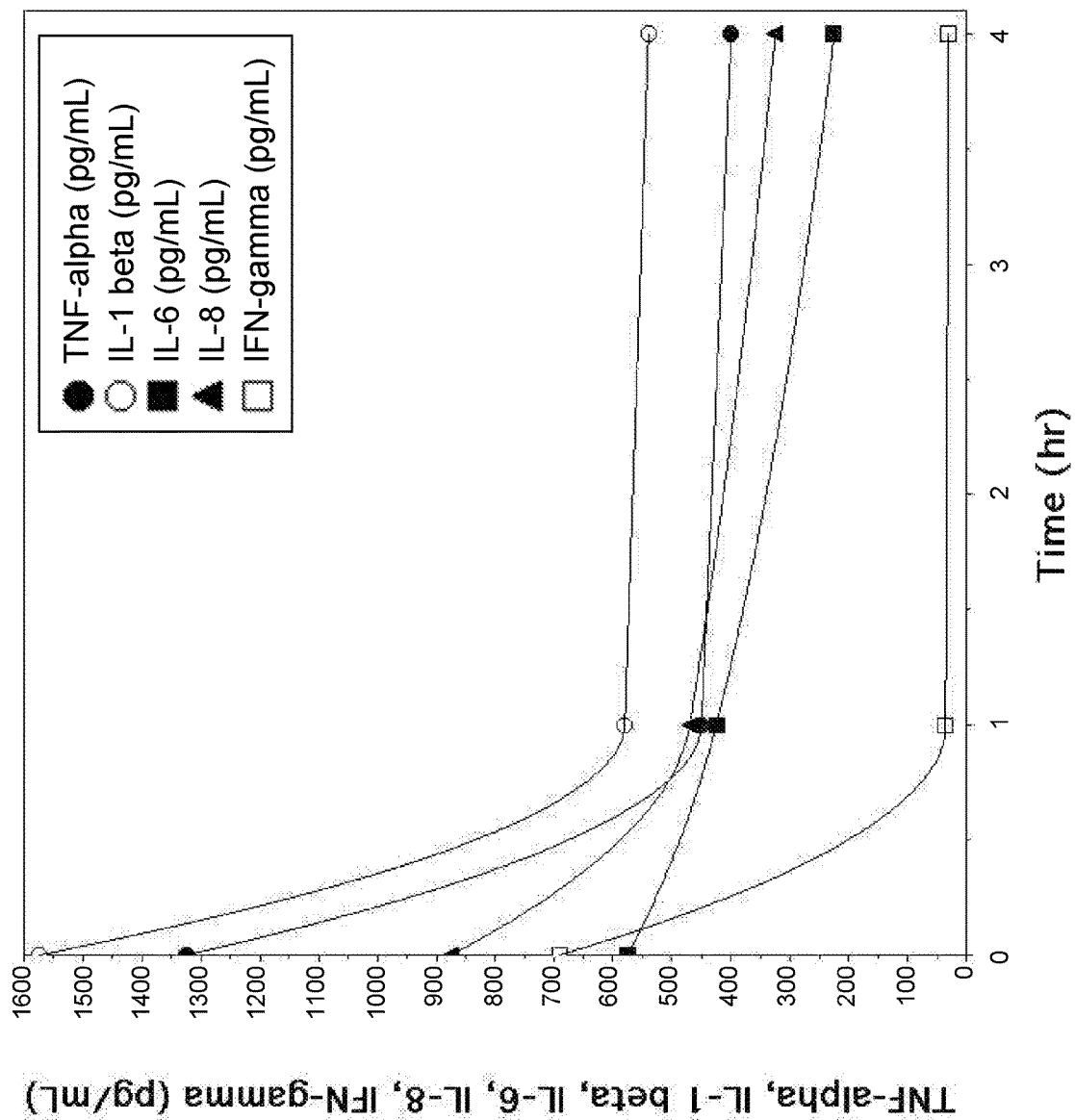

METHOD FOR EXTRACORPOREAL TREATMENT OF PREECLAMPSIA AND RELATED DISORDERS

CROSS-REFERENCE TO RELATED APPLICATIONS

This application is a filing under 35 U.S.C. 371 of International Application No. PCT/US2017/025362 filed Mar. 31, 2017, entitled "Method for Extracorporeal Treatment of Preeclampsia and Related Disorders," which claims priority to U.S. Provisional Patent Application No. 62/316,113 filed Mar. 31, 2016, which applications are incorporated by reference herein in their entirety.

TECHNICAL FIELD

Generally disclosed herein are compositions, systems, and methods for the treatment of subjects experiencing preeclampsia and related disorders. More specifically disclosed herein are methodologies for the extracorporeal reduction of preeclampsia mediators such as angiogenesis inhibitors, vasoconstrictors, reactive oxygen species and inflammatory cytokines from subjects experiencing preeclampsia and related disorders.

BACKGROUND

Preeclampsia is a devastating complication of pregnancy that is a multiorgan disorder associated with significant maternal and neonatal morbidity and mortality. Preeclampsia impacts 5-8% of all births in the United States. The worldwide incidence of preeclampsia can be as high as 10% of pregnancies and approximately 50,000 women die annually from this disease. In the developing world preeclampsia is more common and in parts of Africa as high as 18%. Worldwide, the number of babies who die from preeclampsia is 500,000 per annum.

Preeclamptic symptoms can include hypertension and proteinuria which typically become evident after the 20th week of pregnancy. In the past, edema was considered a diagnostic criterion. Recently, however, it has been eliminated as a requirement for diagnosis. Preeclampsia causes vasospasm, a condition in which your blood vessels squeeze and then relax almost like a muscle spasm. This causes the smooth lining of the blood vessels to become damaged and rough. Once this damage occurs, the body will send out cells to repair the damage. The cells that arrive first are platelets. As platelets and other blood products try to repair the damage, they form little clots along the blood vessel wall causing the blood vessel to become even more narrow, further decreasing blood flow to the organs. The body continually makes new platelets; however, there is a limited supply of platelets in the body at any one time. Once they have become depleted, spontaneous bleeding can occur. Other cells passing by the damaged lining of the blood vessels break open, often spilling their toxic contents. These toxic waste products cause high blood pressure and even more damage to other organs. Vasospasm and the miniature blood clots cause further damage by decreasing blood flow and thus decreasing the oxygen supply to vital organs such as the brain, kidneys, and liver.

The term preeclampsia specifically refers to the disease state before a seizure. Once a woman has had a seizure with this disease, it then becomes eclampsia. Symptoms of preeclampsia include hypertension and proteinuria. Severe preeclampsia is characterized by (1) a systolic blood pressure in a known normotensive woman greater than 140-160 mm Hg or diastolic blood pressure greater than 90-110 mm Hg on 2 occasions at least 6 hours apart in a woman on bed rest and (2) the presence of significant proteinuria. Proteinuria concentrations associated with preeclampsia are in the 300 mg for a 24-hour urine collection. Marked proteinuria is defined as 5 g or more of protein in a 24-hour urine collection. Severe preeclampsia, at times, may be associated with oliguria, cerebral or visual disturbances, pulmonary edema or cyanosis, epigastric or right upper quadrant abdominal pain, impaired liver function, thrombocytopenia, or intrauterine growth restriction. Often, the progression of these symptoms cannot be stopped and full blown toxemia occurs, including kidney failure.

Preeclampsia has a complex pathophysiology with multiple stages. Soluble Fms-like tyrosine kinase-1 (sFlt-1), an antiangiogenic protein, expressed in the second half of pregnancy as the result of placental oxidative stress and inflammation, is an endogenous inhibitor of vascular endothelial growth factor (VEGF) and is responsible for disruption of the maternal endothelium that results in hypertension, proteinuria, and the other systemic manifestations of preeclampsia. Besides sFlt-1, there are other syncytiotrophoblast-derived factors, such as sEndoglin, responsible for maternal systemic inflammatory stress and clinical signs of preeclampsia. The syncytiotrophoblast (SCT) is the outer layer of placenta which is in direct contact with maternal blood. As such it is uniquely positioned to alter maternal hemostasis and endothelial function. Inflammatory cytokines (e.g., TNF-alpha, IL-1 beta, IL6 and IL-8) and vasoconstrictors (e.g., ET-1, TXB2, 8-isoprostane) are additional contributing factors.

The current therapeutic approach to preeclampsia involves monitoring the severity of the disorder and ending the pregnancy, either by induction of labor or cesarean before the symptoms become too severe. Taking into consideration that no definitive preventive strategies or treatment for preeclampsia have been established it is imperative to seek new modalities to treat this serious disorder.

SUMMARY

Disclosed herein is a three-component composition for use in the treatment of preeclampsia and related disorders wherein a first component comprises a bimodal synthetic carbon particle mixture; a second component comprises a first resin bead with at least one affinity ligand directed toward syncytiotrophoblast-derived factor sEndoglin and a third component comprises a second resin bead with at least one affinity ligand directed toward syncytiotrophoblast-derived factor soluble Fms-like tyrosine kinase-1.

Also disclosed herein is a method comprising contacting a bodily fluid with a three-component composition for use in the treatment of preeclampsia and related disorders wherein a first component comprises a bimodal synthetic carbon particle mixture; a second component comprises a first resin bead with at least one affinity ligand directed toward syncytiotrophoblast-derived factor sEndoglin and a third component comprises a second resin bead with at least one affinity ligand directed toward syncytiotrophoblast-derived factor soluble Fms-like tyrosine kinase-1.

BRIEF DESCRIPTION OF THE DRAWINGS

For a more complete understanding of the present disclosure and the advantages thereof, reference is now made to the following brief description, taken in connection with the accompanying figures and drawings and detailed description, wherein like reference numerals represent like parts.

FIG. 9 is a plot of the amount of Tumor Necrosis Factor α (TNF-α), Interleukin 1α (IL-1α), Interleukin 6 (IL-6), Interleukin 8 (IL-8), Interferon γ (IFN-γ) in a sample of blood as a function of time following contact with synthetic bimodal carbon particles comprising a microporous/mesoporous modality as described herein.

DETAILED DESCRIPTION

Figure 1:
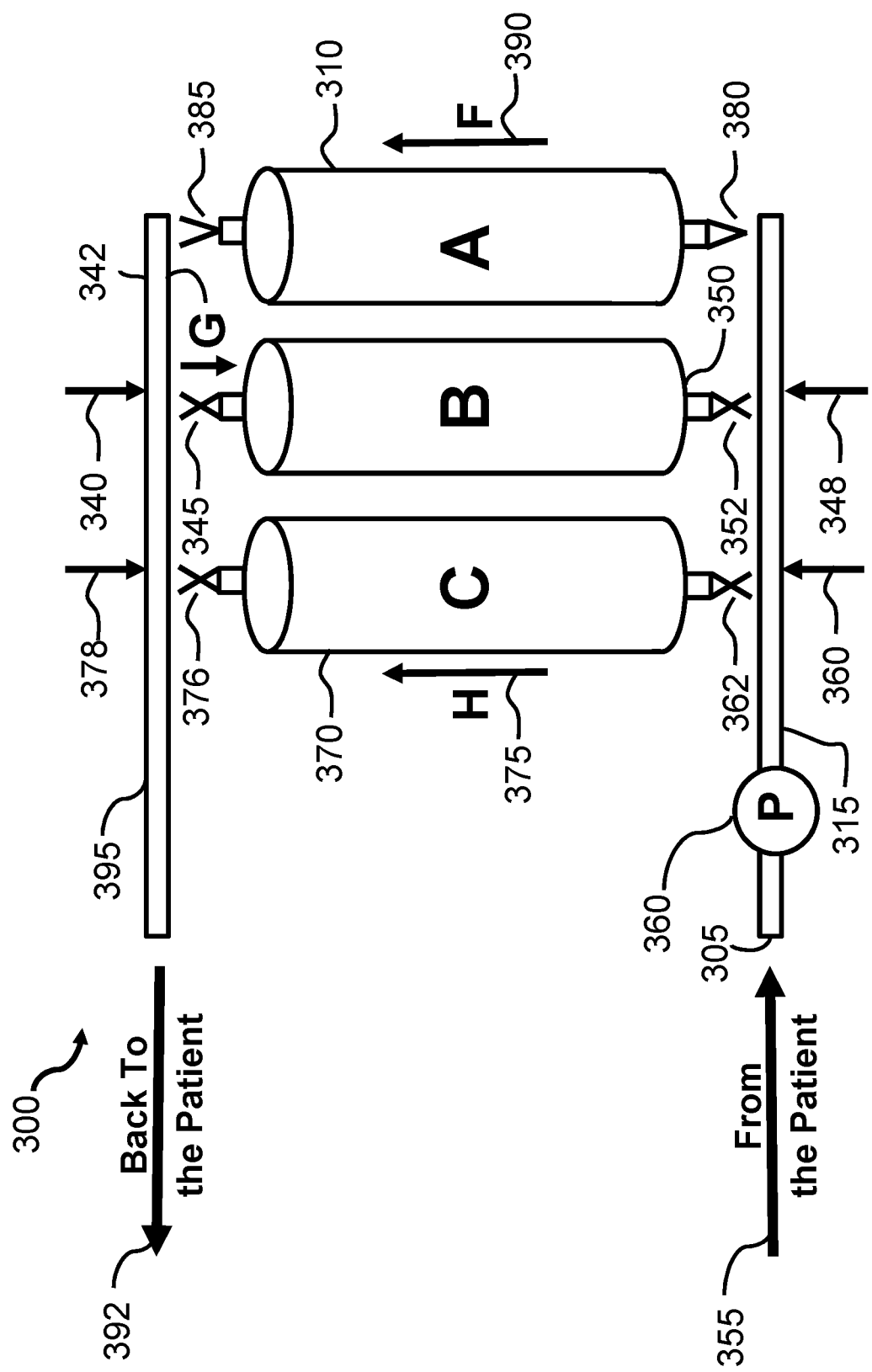
FIG. 1 depicts aspects of a multiple column apparatus as disclosed herein.

Disclosed herein are compositions, systems, and methods for the reduction of mediators of preeclampsia and related disorders in a bodily fluid. Herein "bodily fluids" refer to liquids originating from inside the bodies of living humans. They include fluids that are excreted or secreted from the body. In an aspect, the term "bodily fluid," includes without limitation inter alia plasma without blood cellular components and plasma with blood cellular components (i.e., whole blood). Herein the term "blood cellular components" refers to components such as red corpuscles (erythrocytes), platelets (thrombocytes), and five types of white corpuscles (leukocytes). In an aspect, at least a portion of the bodily fluid is removed from the subject. In an aspect, the bodily fluid comprises whole blood or plasma.

In an aspect, the bodily fluid is whole blood or plasma and the methods disclosed herein comprise contacting at least a portion of a subject's bodily fluid with one or more extracorporeal devices containing a therapeutic formulation of materials designed to reduce the level of circulating mediators of preeclampsia and related disorders. Herein the "therapeutic formulation of materials" refers to a composition of materials that is formulated to address the levels of blood preeclamptic mediators associated with their particular blood profile. The therapeutic formulation of materials may comprise materials such as synthetic carbon particles, resins comprising affinity ligands and the like. As used herein "preeclamptic mediators" refers to any organic or inorganic compound that when present in a subject's blood above a tolerable threshold mediates preeclampsia or related disorders in the subject. Representative examples include, but are not limited to antiangiogenic factors, reactive oxygen species, vasoconstrictors and pro-inflammatory mediators. It is contemplated that the current methodologies may be applied to the treatment of a subject experiencing eclampsia/toxemia.

In an aspect, a method of the present disclosure for treating preeclampsia and related disorders comprises obtaining bodily fluid (e.g., whole blood) from a subject experiencing (i) a second trimester of a pregnancy (ii) a systolic blood pressure greater than 140-160 mm Hg wherein the subject is normortensive; (iii) a diastolic blood pressure greater than 90-110 mm Hg on 2 occasions at least 6 hours apart wherein the subject has been resting; (iv) the amount of protein in a urine sample of equal to or greater than about 300 mg/24 hour collection period; or (v) combinations thereof. Herein normortensive refers to having a normal blood pressure. The normal blood pressure for the subject may be determined based on empirical data obtained using any suitable methodology the ordinarily skilled artisan such as a health care professional taking blood pressure readings and/or obtaining such readings based on a subjects medical records. Herein resting refers to bed rest which will differ from subject to subject and may range from simple periodic resting at home to full bed rest with monitoring in a hospital setting.

Aspects of the present disclosure are methods comprising contacting a bodily fluid, for example a bodily fluid comprising whole blood or plasma with a therapeutic formulation comprising (i) at least two resins with affinity ligands directed toward syncytiotrophoblast-derived factors and (ii) synthetic bimodal carbon particles ("SBCP").

Aspects of the present disclosure also include methods comprising contacting a bodily fluid, for example a bodily fluid comprising whole blood or plasma with a therapeutic formulation comprising (i) a first resin (e.g., resin bead) comprising an attached affinity ligand directed toward a first syncytiotrophoblast-derived factor; (ii) a second resin (e.g., resin bead) comprising an attached affinity ligand directed toward a second syncytiotrophoblast-derived factor; and (iii) synthetic bimodal carbon particles.

Aspects of the present disclosure also include methods comprising contacting a bodily fluid, for example a bodily fluid comprising whole blood or plasma with a therapeutic formulation comprising (i) a first resin (e.g., resin bead) comprising an attached affinity ligand directed toward a first syncytiotrophoblast-derived factor, wherein the resin is an cation exchange resin ("CER"); (ii) a second resin (e.g., resin bead) comprising an attached affinity ligand directed toward a second syncytiotrophoblast-derived factor, wherein the resin is an anion exchange resin ("AER")); and (iii) synthetic bimodal carbon particles.

In an aspect, one or more of the therapeutic formulation components may act as a chromatographic material. For example, one or more components of the therapeutic formulation may act as an adsorbent. Herein, the term "adsorbent" is used for simplicity and it is to be understood the term "adsorbent" does not necessarily refer to the mechanism of action of the material.

Additional aspects of the present disclosure are devices containing a therapeutic formulation of the type disclosed herein. It is contemplated that the therapeutic formulation may be optimized for use in a particular device depending on the end-use application of the device.

With reference to FIG. 1, a methodology of the type disclosed herein comprises establishing fluid communication between a subject's blood flow as accessed through a jugular, subclavian or femoral vein with double lumen catheter of the subject 355 and the inlet 305 of the apparatus 300. Other options are chronic vascular accesses used in hemodialysis that are created by an earlier surgical procedure: (i) native arteriovenous fistulas (native AVFs), (ii) arteriovenous shunts using graft material (AV graft), and (iii) tunnelled double-lumen catheters. The pump 360 regulates the flow of the subject's blood to the remainder of the apparatus 300 through conduit 315. Conduit 315 may be a pipe or flow line comprised of material suitable for use in the methodologies disclosed herein. In an aspect, the subject's blood is allowed to flow through conduit 315 until it reaches valve 380 which when in the on position allows the blood flow to enter column A 310 in a particular flow direction F 390. Blood may be pumped through column A 310 and exit the column thorough an outlet regulated by a valve 385. Blood exiting from column A 310 through the outlet regulated by valve 385 may enter conduit 395 where it is pumped to inlet port 340 whose access is regulated by valve 345. When valve 345 is in the on position, the blood may be pumped from inlet port 340 to column B 350 where it moves in flow direction G 342 through column B 350 to outlet port 348 which is regulated by valve 352. When valve 352 is in the on position the blood may flow from column B 350 into conduit 315. In an aspect, the subject's blood is allowed to flow through conduit 315 until it reaches inlet port 360 which is regulated by valve 362 which when in the on position allows the blood flow to enter column C 370 in a particular flow direction H 375. The blood may exit column C 370 via outlet port 378 which is regulated by valve 376 which when in the on position allows the blood to flow into conduit 395 and back to the jugular, subclavian or femoral vein, or the vascular accesses that are created by an earlier surgical procedure: (i) native arteriovenous fistulas (native AVFs), (ii) arteriovenous shunts using graft material (AV graft), and (iii) tunnelled double-lumen catheters, of the subject 392.

Components of a therapeutic formulation of the type disclosed herein may be housed in column A 310, column B 350 and column C 370 and may comprise (i) at least two resins with affinity ligands directed toward syncytiotrophoblast-derived factors and (ii) an SBCP. In an aspect, subsequent to contacting a first sample comprising whole blood or plasma with the therapeutic formulation a second sample having a reduced level of preeclamptic mediators when compared to the first sample comprising either whole blood or plasma is recovered and may then be administered to a subject in need thereof. The term "subject," as used herein, comprises any and all organisms and includes the term "patient." In some aspects, a treatment methodology comprises having the subject in communication with an extracorporeal device of the type disclosed herein such that (a) removal of the blood, (b) treatment of the blood, and (c) return of the second sample having a reduced level of preeclamptic mediators when compared to the first sample comprising either plasma or whole blood is carried out with the use of a device that allows the patient to remain in contact with or proximate to the device during the entire procedure. In an alternative aspect, the method comprises collecting a first sample comprising either plasma or whole blood from a subject; and contacting the first sample with the therapeutic formulation distal to the patient. The second sample may then be administered to the patient.

In an aspect, a component of the therapeutic formulation is a resin bead with at least one affinity ligand directed toward the syncytiotrophoblast-derived factor sFlt-1. The term "soluble (s)Flt-1" as used herein refers to polypeptides which are a soluble form of the VEGF receptor FLT1 that were identified in conditioned culture medium of human umbilical vein endothelial cells. The endogenous soluble FLT1 receptor is chromatographically and immunologically similar to recombinant human sFLT1 and binds VEGF with a comparable high affinity. Human sFlt-1 is shown to form a VEGF-stabilized complex with the extracellular domain of KDR/Flk-1 in vitro. Herein sFlt-1 refers to human sFlt-1 or a variant thereof. Alternatively, human sFlt-1 can be deduced from the amino acid sequence of sFlt-1 as obtained from the gene sequence found in Genebank accession number P17948, GI: 125361. It is to be understood that a variant as referred to in accordance with the present disclosure shall have an amino acid sequence which differs due to at least one amino acid substitution, deletion and/or addition wherein the amino acid sequence of the variant is still at least 50%, 60%, 70%, 80%, 85%, 90%, 92%, 95%, 97%, 98%, or 99% identical with the amino sequence of the specific sFlt-1. Variants may be allelic variants, splice variants or any other species specific homologs, paralogs, or orthologs. Moreover, the variants referred to herein include fragments of the specific sFlt-1 or the aforementioned types of variants as long as these fragments have the essential immunological and biological properties that contribute to the preeclamptic event. Such fragments may be, e.g., degradation products of sFlt-1. Further included are variants which differ due to posttranslational modifications such as phosphorylation, glycosylation or myristylation.

In an aspect, a component of the therapeutic formulation is a resin bead with at least one affinity ligand directed toward the syncytiotrophoblast-derived factor sEndoglin (sEng). sEndoglin, also called CD105, is a homodimeric transmembrane glycoprotein primarily associated with the human endometrium Mutations in the endoglin gene are responsible for the hereditary hemorrhagic telangiectasia type 1 (HHT1), also known as Osler-Weber-Rendu syndrome. This is an autosomal dominant vascular disorder probably caused by a haploinsufficiency mechanism displaying low levels of the normal protein. sEng inhibits formation of capillary tubes in vitro and induces vascular permeability and hypertension in vivo. sEng impairs binding of TGF-β1 to its receptors and downstream signaling including effects on activation of NOS and vasodilation, suggesting that sEng leads to dysregulated TGF-β signaling in the vasculature. Herein sEng refers to human sEng or a variant thereof. Alternatively, human sEng can be deduced from the amino acid sequence of sEng as obtained from the gene sequence found in the Ensembl database: ENG ENSG00000106991. It is to be understood that a variant as referred to in accordance with the present disclosure shall have an amino acid sequence which differs due to at least one amino acid substitution, deletion and/or addition wherein the amino acid sequence of the variant is still at least 50%, 60%, 70%, 80%, 85%, 90%, 92%, 95%, 97%, 98%, or 99% identical with the amino sequence of the specific sEng. Variants may be allelic variants, splice variants or any other species specific homologs, paralogs, or orthologs. Moreover, the variants referred to herein include fragments of the specific sEng or the aforementioned types of variants as long as these fragments have the essential immunological and biological properties that contribute to the preeclamptic event. Such fragments may be, e.g., degradation products of sEng. Further included are variants which differ due to posttranslational modifications such as phosphorylation, glycosylation, or myristylation.

In an aspect, a therapeutic formulation comprises a material to reduce or eliminate the amount of sFlt-1 or sEng present in the first sample comprising either plasma or whole blood obtained from the subject. Any material able to reduce the amount of sFlt-1 or sEng present and compatible with the other components and methodologies of the present disclosure may be utilized. In an aspect, the material is a resin conjugated with an affinity ligand directed to sFlt-1, sEng, or both.

In an aspect, a therapeutic formulation of the type disclosed herein comprises a first resin with an affinity ligand for binding sFlt-1. In an aspect, a therapeutic formulation of the type disclosed herein comprises a second resin with an affinity ligand for binding sEng. The affinity ligand can be any compound, e.g., a peptide, polypeptide, nucleic acid, or small molecule, binding to the polypeptide described herein. For example the affinity ligand can include without limitation antibodies, nucleic acids, peptides or polypeptides such as receptors or binding partners for the polypeptide and fragments thereof comprising the binding domains for the syncytiotrophoblast-derived factor.

In an aspect, the affinity ligand is an antibody. Herein "antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

Affinity ligands suitable for use in the present disclosure may be prepared using any suitable methodology. In an alternative aspect, affinity ligands suitable for use in the present disclosure are commercially available. For example, identification and production of suitable antibodies or aptamers is also offered by commercial suppliers. The person skilled in the art is familiar with methods to develop derivatives of such ligands with higher affinity or specificity. These derivatives can then be tested for binding according to screening procedures such as phage display.

In an aspect, the ligand or agent binds specifically to the polypeptide. Specific binding according to the present disclosure means that the ligand or agent should not bind substantially to ("cross-react" with) another peptide, polypeptide or substance present in the sample to be analyzed. Alternatively, the specifically bound material should be bound with at least 3 times higher, alternatively at least 10 times higher or alternatively at least 50 times higher affinity than any other relevant material. Non-specific binding may be tolerable, if it can still be distinguished and measured unequivocally, e.g. according to its size on a Western Blot, or by its relatively higher abundance in the sample. In this technology both monoclonal and polyclonal anti-sFlt-1 and anti-sEndoglin/CD105 can be used. The use of polyclonal antibody is warranted by its extracorporeal therapeutic utilization. Unconjugated Anti-sFlt1 antibody reactive with human antigen can be obtained commercially from many suppliers such as LifeSpan BioSciences (Anti-FLT1/VEGFR1 Antibody; Seattle, WA), R&D Systems (VEGF R1/Flt-1 Antibody; Minneapolis, MN), ProSci, Inc (FLT-1 Antibody; Fort Collins, CO). Commercially available unconjugated sEndoglin/CD 105 antibody reactive with human antigen can be purchased from various vendors preferably from BioLegend (CD105 (Endoglin) Antibody; San Diego, CA), ProSci, Inc (Endoglin Antibody; Fort Collins, CO), MBL International (Anti-CD 105 (Endoglin) mAb; Woburnma, MA).

In an aspect, a component of the therapeutic formulation is a resin bead with affinity ligands directed toward the syncytiotrophoblast-derived factor sEng. In an aspect, a component of the therapeutic formulation is a resin bead with affinity ligands directed toward the syncytiotrophoblast-derived factor sFlt-1. The resin bead may be comprised of any material able to associate with an affinity ligand of the type disclosed herein and compatible with the compositions and methodologies disclosed herein.

In an aspect, the resin and/or resin bead comprises gelatin, alginate, collagen type I, fibrin glue, polyglycerol sebacate (PGS), polyglycolic acid (PGA), poly-1-lactide (PLA), poly (lactide-co-glycolide) (PLGA), polyvinyl alcohol (PVA), polycaprolactone, poly(N-isopropylacrylamide), polyethylene (PE), sepharose; silica; polyoxymethylene (POM), polypropylene (PP), polyvinylchloride (PVC), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers or combinations thereof. In an alternative aspect, the resin comprises PVA.

Figure 3:
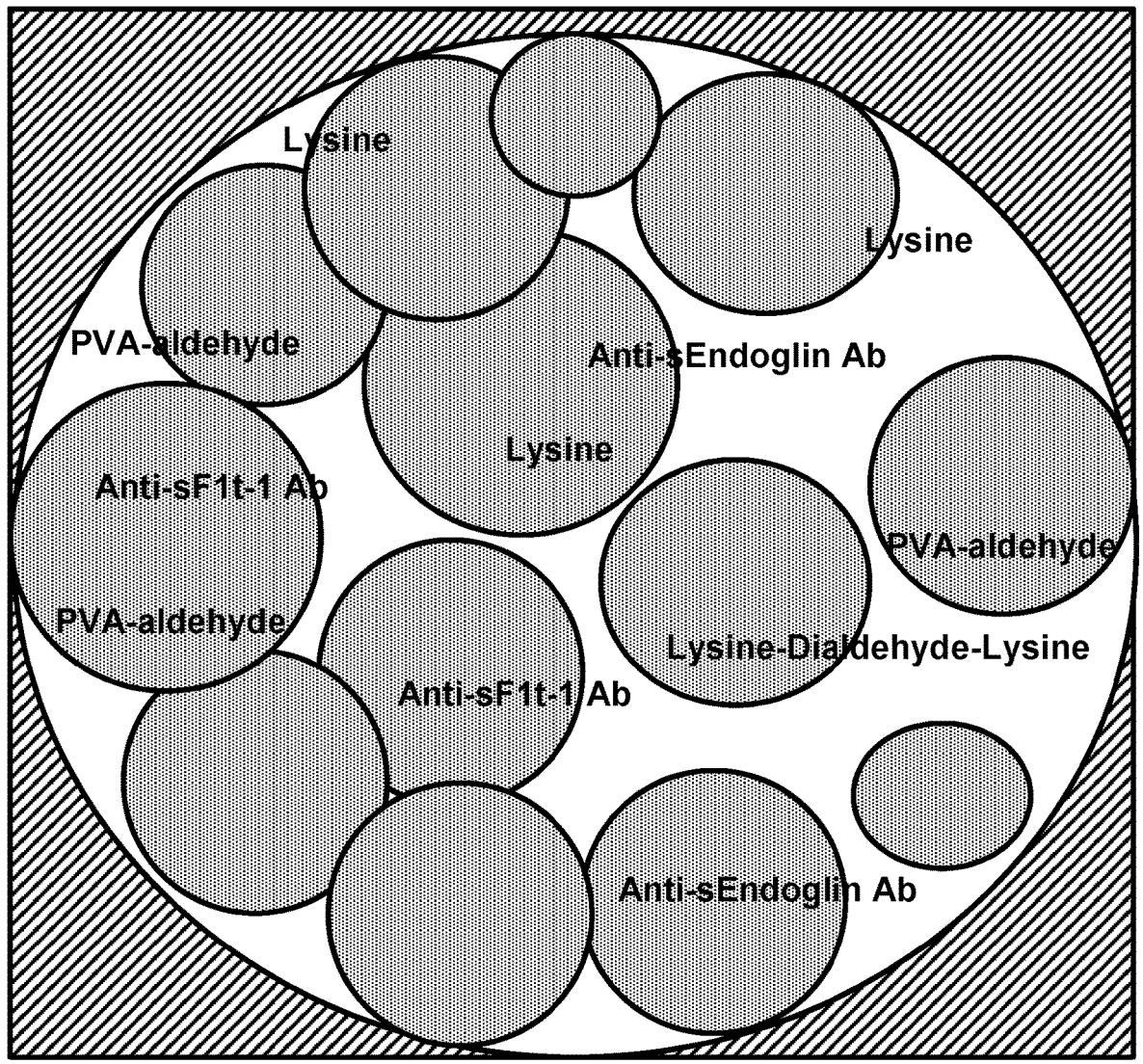
FIG. 3 depicts aspects of immobilized antibodies onto modified polyvinyl alcohol (PVA).

In some aspects, the resin and/or resin bead is functionalized using any suitable methodology such that the resin can be associated with an affinity ligand of the type disclosed herein (for example as shown in FIG. 3). For example, a strategy for the functionalization of polymer is via copolymerization with functional monomers (e.g. alcohols, carboxylic acids, amines, acrylates). Another strategy for the functionalization of polymers is post-polymerization functionalization, which is the modification of the polymer after the polymerization process. Post-polymerization techniques might include without limitation targeting functional groups present in the polymer via carbodiimide or UV-initiated radical coupling, or non-specific, using azide- or glutaraldehyde-based couplings.

In an aspect, the therapeutic formulation comprises a resin bead which may be present in a plurality of bead sizes. Resin beads of the type useful in the present disclosure may be charged or neutral. For example, resin beads suitable for use in the present disclosure may comprise positively, negatively and/or uncharged beads having particle sizes ranging from about 1 mm to about 12 mm. In some aspects, beads with particle sizes greater than about 1 mm may comprise up to about 50% by volume of the therapeutic formulation of materials with respect to the volume of carbon present in the therapeutic formulation of materials.

In an aspect, the resin beads may be negatively charged large beads (e.g., greater than about 1 mm particle size) and comprise materials such as polytetrafloroethylene (TEFLON) or polyamideimide (TORLON). In an aspect, the resin beads may be positively charged large beads (e.g., greater than about 1 mm particle size) and comprise materials such as polyamide 6/6 (Nylon) and polyoxymethylene (DELRIN). In an aspect, the resin beads may be uncharged large beads (e.g., greater than about 1 mm particle size) and comprise materials such as polystyrene, polysulfone, as well as uncharged glass, ceramic and metal beads.

In an aspect, the therapeutic formulation comprises a carbonaceous material. In an aspect, the adsorbent material comprises a bimodal synthetic carbon particle (SBCP) containing micro-, meso- and macropores from porous phenolic resins. As used herein, the term "micropore" refers to a pores with diameter<2 nm, as measured by nitrogen adsorption and mercury porosimetry methods and as defined by IUPAC. As used herein, the term "mesopore" refers to pores with diameter from ca. 2 nm to ca. 50 nm, as measured by nitrogen adsorption and mercury porosimetry methods and as defined by IUPAC. As used herein, the term "macropore" refers to pores with diameters larger than 50 nm, as measured by nitrogen adsorption and mercury porosimetry methods and as defined by IUPAC. In relation to this invention there are two types of macropores. In macroporous beads they are located within beads and formed by pore-formers. Their size is 50-500 nm, typically 70-200 nm. These macropores are very effective in adsorption of cytokines. Typically a precursor resin formulation is used which comprises a large proportion of pore former, e.g. 250 parts ethylene glycol or other pore former to 100 parts of resin-forming components Herein a mesoporous resin may be formed by condensing a nucleophilic component which comprises a phenolic compound or a phenol condensation prepolymer with at least one electrophilic cross-linking agent selected from formaldehyde, paraformaldehyde, furfural and hexamethylene tetramine in the presence of a pore-former selected from the group consisting of a diol (e.g. ethylene glycol), a diol ether, a cyclic ester, a substituted cyclic ester, a substituted linear amide, a substituted cyclic amide, an amino alcohol and a mixture of any of the above with water to form a resin. The pore-former is present in an amount effective to impart meso- or macroporosity to the resin (e.g. at least 120 parts by weight of the pore former being used to dissolve 100 parts by weight of the total resin forming components, i.e. nucleophilic component plus electrophilic component), and it is removed from the porous resin after condensation by cascade washing with water or by vacuum drying. The resulting resin may be carbonised by heating in an inert atmosphere to a temperature of at least 600° C. to give a material having a bimodal distribution of pores, the pore structure as estimated by nitrogen adsorption porosimetry comprising micropores and mesopores or macropores. The value for the differential of pore volume with respect to the logarithm of pore radius (dV/d log R) for the mesopores is greater than 0.2 for at least some values of pore size in the range 20-500 Å. The mesoporous carbon may have a BET surface area of 250-800 $m^2/g$ without activation. It may be activated by heating it at high temperature in the presence of carbon dioxide, steam or a mixture thereof, e.g. by heating it in carbon dioxide at above 800° C., or it may be activated by heating it in air at above 400° C. It may then have surface areas of up to 2000 $m^2/g$ and even higher e.g. 1000-2000 $m^2/g$. As used herein the term "BET surface area" is determined by the Brunauer, Emmett, and Teller (BET) method according to ASTM D1993-91, see also ASTM D6556-04.

Resins for making carbonaceous material can be prepared from any of the starting materials such that the nucleophilic components may comprise phenol, bisphenol A, alkyl phenols e.g. cresol, diphenols e.g. resorcinol and hydroquinione and aminophenols e.g. m-amino-phenol.

It is preferred to use as nucleophilic component a phenolic novolac or other similar oligomeric starting material which because it is already partly polymerized makes polymerization to the desired resin a less exothermic and hence more controllable reaction. The preferred novolacs have average molecular weights (AMW) in the range of from 300 to 3000 prior to cross-linking (corresponding to a DP with respect to phenol of about 3-30). Where novolac resins are used, they may be solids with melting points in the region of 100° C. Novolac resins of AMW less than 2000 and preferably less than 1500 form resins which on carbonisation tend to produce carbons with desired pore size distributions using lower amounts of pore former. Novolacs are thermally stable in that they can be heated so that they become molten and cooled so that they solidify repeatedly without structural change. They are cured on addition of cross-linking agents and heating. Fully cured resins are infusible and insoluble. Whilst commercial novolacs are largely produced using phenol and formaldehyde, a variety of modifying reagents can be used at the pre-polymer formation stage to introduce a range of different oxygen and nitrogen functionalities and cross-linking sites. These include but are not limited to: (a) Dihydric phenols e.g. resorcinol and hydroquinone. Both are more reactive than phenol and can lead to some cross-linking at the pre-polymer production stage. It is also possible to introduce these compounds at the cross-linking stage to provide different cross-linking paths. These also increase the oxygen functionality of the resins. (b) Nitrogen containing compounds that are active in polycondensation reactions, such as urea, aromatic (aniline, m-amino phenol) and heteroaromatic (melamine) amines. These allow the introduction of specific types of nitrogen functionality into the initial polymer and final carbon and influence the development of the mesoporous structure of both the resins and the final carbons. Like hydroquinone and resorcinol, all the nitrogen containing nucleophilic modifying reagents which can be used possess two or more active sites and are more reactive in condensation reactions than phenol or novolacs. It means that they are first to react with primary cross-linking agents forming secondary cross-linking agents in situ.

The nucleophilic component may be provided alone or in association with a polymerization catalyst which may be a weak organic acid miscible with the novolac and/or soluble in the pore former e.g. salicylic acid, oxalic acid or phthalic acid. The concentration of novolac in the pore former may be such that when combined with the solution of cross-linking agent in the same pore former the overall weight ratio of pore former to (novolac+cross-linking agent) is at least 125:100 by weight. The actual ratios of novolac:pore former and cross-linking agent:pore former are set according to convenience in operation by the operational requirements of a bead production plant and are controlled by the viscosity of the novolac:pore former solution such that it remains pumpable and by the ratio of cross-linking agent:pore former such that the cross-linking agent remains in solution throughout the plant.

The cross-linking agent is normally used in an amount of from 5 to 40 parts by weight (pbw) per 100 parts by weight of the nucleophilic components e.g. novolac. It may be, for example, an aldehyde e.g. formaldehyde or furfural, it could be hexamethylenetetramine (hexamine), or hydroxymethylated melamine.

Hexamine is preferably used as cross-linking agent. In aspects requiring a completely cured resin, it is preferably used for cross-linking novolac resin at a proportion of 10 to 25 pbw e.g. about 15 to 20 pbw hexamine per 100 pbw of novolac. This ensures formation of the solid resin with maximal cross-linking degree and ensures the stability of the mesopore structure during subsequent removal of the pore former.

The pore former also acts as solvent. Thus, the pore former is preferably used in sufficient quantities to dissolve the components of the resin system, the weight ratio of pore former to the total components of the resin system resin being preferably at least 1.25:1.

The pore former may be, for example, a diol, a diol-ether, a cyclic ester, a substituted cyclic or linear amide or an amino alcohol e.g. ethylene glycol, 1,4-butylene glycol, diethylene glycol, triethylene glycol, γ-butyrolactone, propylene carbonate, dimethylformamide, N-methyl-2-pyrrolidinone and monoethanolamine, ethylene glycol being preferred, and where the selection is also limited by the thermal properties of the solvent as it should not boil or have an excessive vapour pressure at the temperatures used in the curing process.

It is thought that the mechanism of meso- and macropore generation is due to a phase separation process that occurs during the cross-linking reaction. In the absence of a pore former, as the linear chains of pre-polymer undergo cross-linking, their molecular weight initially increases. Residual low molecular weight components become insoluble in the higher molecular weight regions causing a phase separation into cross-linked high molecular weight domains within the lower molecular weight continuous phase. Further condensation of light components to the outside of the growing domains occurs until the cross-linked phase becomes essentially continuous with residual lighter pre-polymer trapped between the domains. In the presence of a low level of pore former the pore former is compatible with, and remains within, the cross-linked resin domains, (e.g., <120 parts/100 parts Novolac for the Novolac-Hexamine-Ethylene Glycol reaction system), whilst the remainder forms a solution with the partially cross-linked polymer between the domains. In the presence of higher levels of pore former, which exceed the capacity of the cross-linked resin, the pore former adds to the light polymer fraction increasing the volume of material in the voids between the domains that gives rise to the mesoporosity and/or macroporosity. In general, the higher the pore former content, the wider the mesopores, up to macropores, and the higher the pore volume.

This phase separation mechanism provides a variety of ways of controlling the pore development in the cross-linked resin structures. These include chemical composition and concentration of the pore former; chemical composition and quantity of the cross-linking electrophilic agents, presence, chemical nature and concentration of modifying nucleophilic agents, chemical composition of phenolic nucleophilic components (phenol, novolac), the presence of water within the solvent and concentration of any curing catalyst if present.

An SBCP suitable for use in the present disclosure may have any shape compatible with the compositions and methodologies disclosed herein. For example the shape of the SBCP may be that of an irregular granule, a low angularity shape, spherical (e.g., bead), pellet, minilith, monolith, etc. For simplicity, the present disclosure may refer to the use of beads of the SCB however it is to be understood the SBCP may be of any suitable shape.

Production of the bead form may be by pouring a solution of a partially cross-linked pre-polymer into a hot liquid such as mineral oil containing a dispersing agent and stirring the mixture. The pre-polymer solution forms into beads which are initially liquid and then, as curing proceeds, become solid. The average bead particle size is controlled by several process parameters including the stirrer type and speed, the oil temperature and viscosity, the pre-polymer solution viscosity and volume ratio of the solution to the oil and the mean size can be adjusted between 5 and 2000 µm although in practice the larger bead sizes are difficult to achieve owing to problems with the beads in the stirred dispersion vessel. The beads can then be filtered off from the oil. In a preparative example, industrial novolac resin is mixed with ethylene glycol at an elevated temperature, mixed with hexamine and heated to give a viscous solution which is poured into mineral oil containing a drying oil, after which the mixture is further heated to effect curing. On completion of curing, the reaction mixture is cooled, after which the resulting porous resin is filtered off, and washed with hot water to remove pore former and a small amount of low molecular weight polymer. The cured beads are carbonized to porous carbon beads which have a pore structure as indicated above, and may be activated as indicated above. It is stated that the beads can be produced with a narrow particle size distribution e.g. with a D90/D10 of better than 10 and preferably better than 5. However, the bead size distribution that can be achieved in practice in stirred tank reactors is relatively wide, and the more the process is scaled up the worse the homogeneity of the mixing regime and hence the particle size distribution becomes wider.

Discrete solid beads of polymeric material e.g. phenolic resin having a porous structure may be formed, which process may produce resin beads on an industrial scale without aggregates of resin building up speedily and interrupting production. The process comprises the steps of: (a) combining a stream of a polymerizable liquid precursor e.g. a novolac and hexamine as cross-linking agent dissolved in a first polar organic liquid e.g. ethylene glycol with a stream of a liquid suspension medium which is a second non-polar organic liquid with which the liquid precursor is substantially or completely immiscible e.g. transformer oil containing a drying oil; (b) mixing the combined stream to disperse the polymerizable liquid precursor as droplets in the suspension medium e.g. using an in-line static mixer; (c) allowing the droplets to polymerise in a laminar flow of the suspension medium so as to form discrete solid beads that cannot agglomerate; and (d) recovering the beads from the suspension medium.

For bead production, the pore former comprises a polar organic liquid e.g. ethylene glycol chosen in combination with dispersion medium which is a non-polar organic liquid so as to form a mainly or wholly immiscible combination, the greater the incompatibility between the pore former which forms the dispersed phase and the dispersion medium, the less pore former becomes extracted into the dispersion medium. The pore former desirably has a greater density than the dispersion medium with which it is intended to be used so that droplets of the pore former containing dissolved resin-forming components will pass down a column more rapidly than a descending flow of dispersion medium therein. Both protic and aprotic solvents of different classes of organic compounds match these requirements and can be used as pore formers, both individually and in mixtures. In addition to dissolving the reactive components and any catalyst, the pore former should also, in the case of phenolic resins, be compatible with water and/or other minor condensation products (e.g. ammonia) which are formed by elimination as polymerization proceeds, and the pore former is preferably highly miscible with water so that it can be readily removed from the polymerized resin beads by washing.

The dispersion medium is a liquid which can be heated to the temperature at which curing is carried out e.g. to 160° C. without boiling at ambient pressure and without decomposition and which is immiscible with ethylene glycol and with the dissolved components therein. It may be hydrocarbon-based transformer oil which is a refined mineral oil and is a by-product of the distillation of petroleum. It may be composed principally of $C_{15}$-$C_{40}$ alkanes and cycloalkanes, have a density of 0.8-0.9 depending upon grade and have a boiling point at ambient pressure of 260-330° C., also depending upon grade. Transformer oil has a viscosity of about 0.5 poise at 150° C. which is a typical cure temperature. Transformer oil or other dispersion medium may be used in volumes 3-10 times the volume of the combined streams of nucleophilic precursor and crosslinking agent e.g. about 5 times.

Preferred dispersing agents which are dissolved in the dispersion medium before that medium is contacted with the reaction mixture to be dispersed therein to retard droplet coalescence are either sold as drying oils e.g. Danish oil or are produced by partially oxidizing naturally occurring precursors such as tung oil, linseed oil etc. The dispersing agents are consumed as the process proceeds, so that if the dispersion medium is recycled, dispersing agent in the recycled oil stream should be replenished. The dispersing agent is conveniently supplied as a stream in solution in the dispersion medium e.g. transformer oil and e.g. in an amount of 5-10% v/v where Danish oil is used which contains a low concentration of the active component to give final concentration of the dispersant in the dispersion medium 0.2-1% v/v. Higher dispersant concentrations would be used in the case of oxidised vegetable oils.

The resin beads formed as described above may be carbonised and optionally activated. For example, carbonization and activation may comprise supplying the material to an externally fired rotary kiln maintained at carbonizing and activating temperatures, the kiln having a downward slope to progress the material as it rotates, the kiln having an atmosphere substantially free of oxygen provided by a counter-current of steam or carbon dioxide, and annular weirs being provided at intervals along the kiln to control progress of the material. In an aspect, a SBCP suitable for use in the present disclosure is characterized by a microporous/macroporous structure. In an aspect, a SBCP suitable for use in the present disclosure is characterized by a microporous/mesoporous structure. In an aspect, a SBCP suitable for use in the present disclosure is characterized by a mesoporous/macroporous structure.

Figure 4:
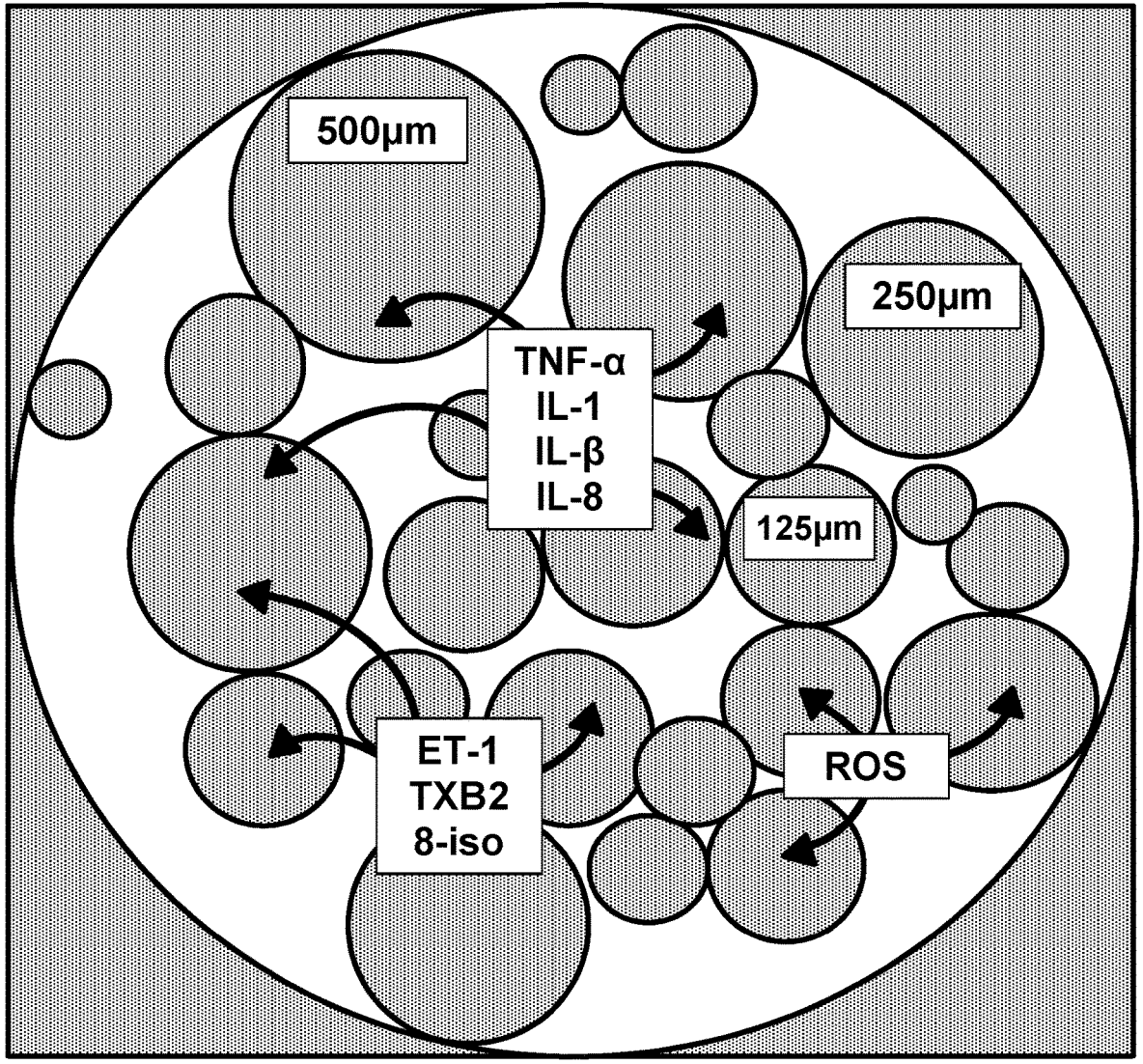
FIG. 4 depicts aspects of synthetic functionalized carbon material in which pore size is controlled as described herein.
Figure 5:
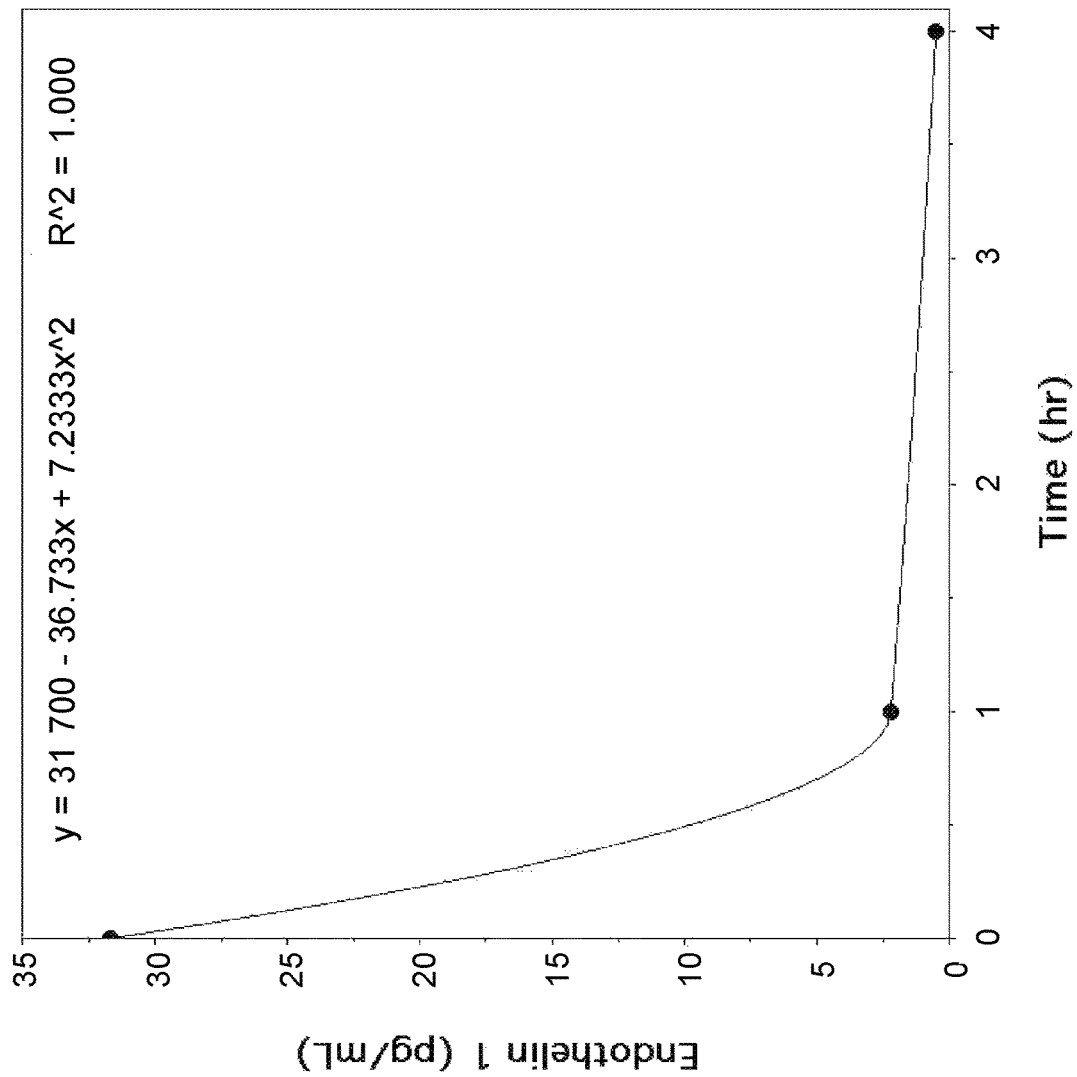
FIG. 5 is a plot of the amount of endothelin-1 (ET-1) in a sample of blood as a function of time following contact with synthetic bimodal carbon particles comprising a microporous/mesoporous modality as described herein.
Figure 6:
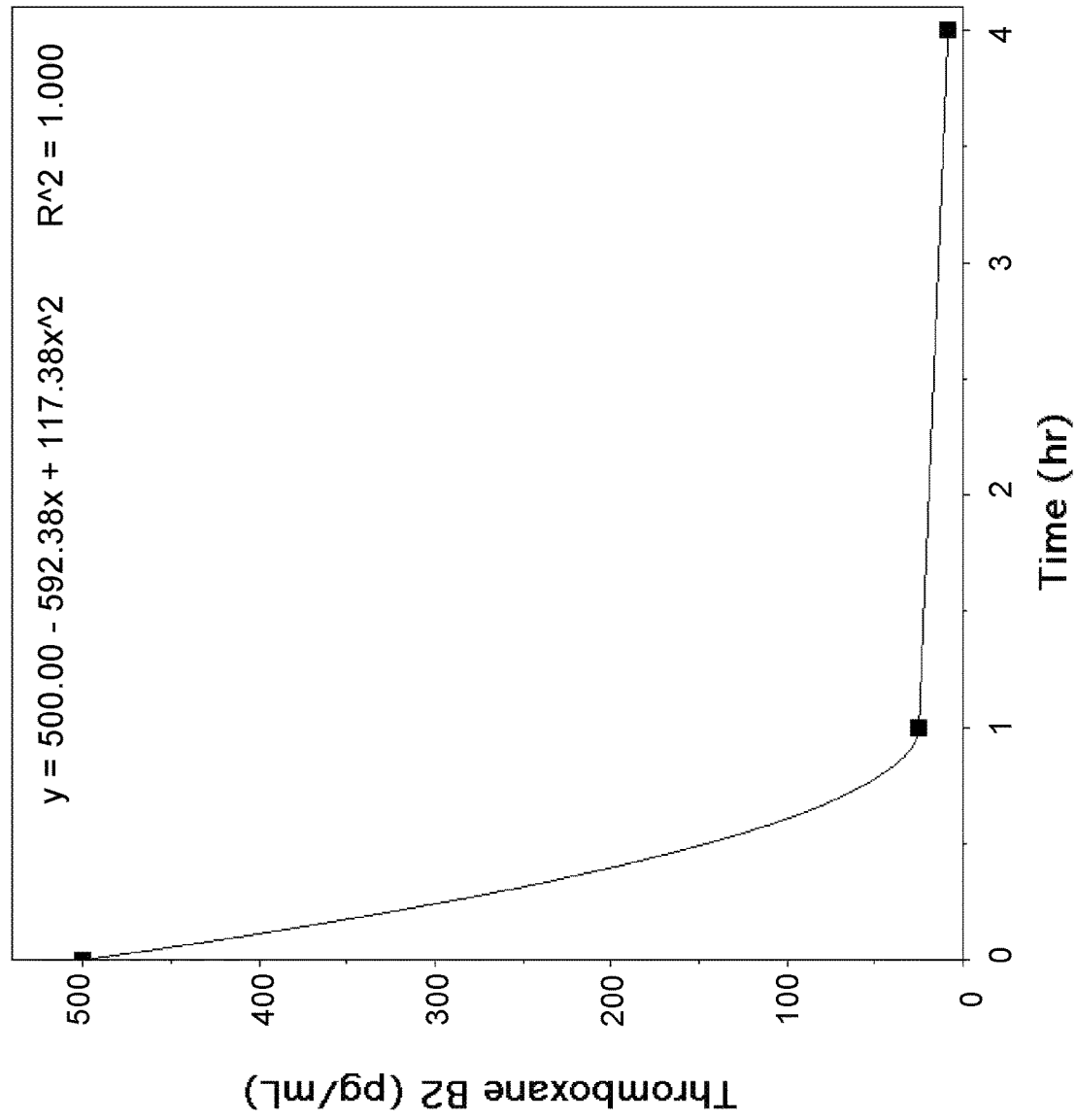
FIG. 6 is a plot of the amount of thromboxane B2 (TXB2) in a sample of blood as a function of time following contact with synthetic bimodal carbon particles comprising a microporous/mesoporous modality as described herein.
Figure 7:
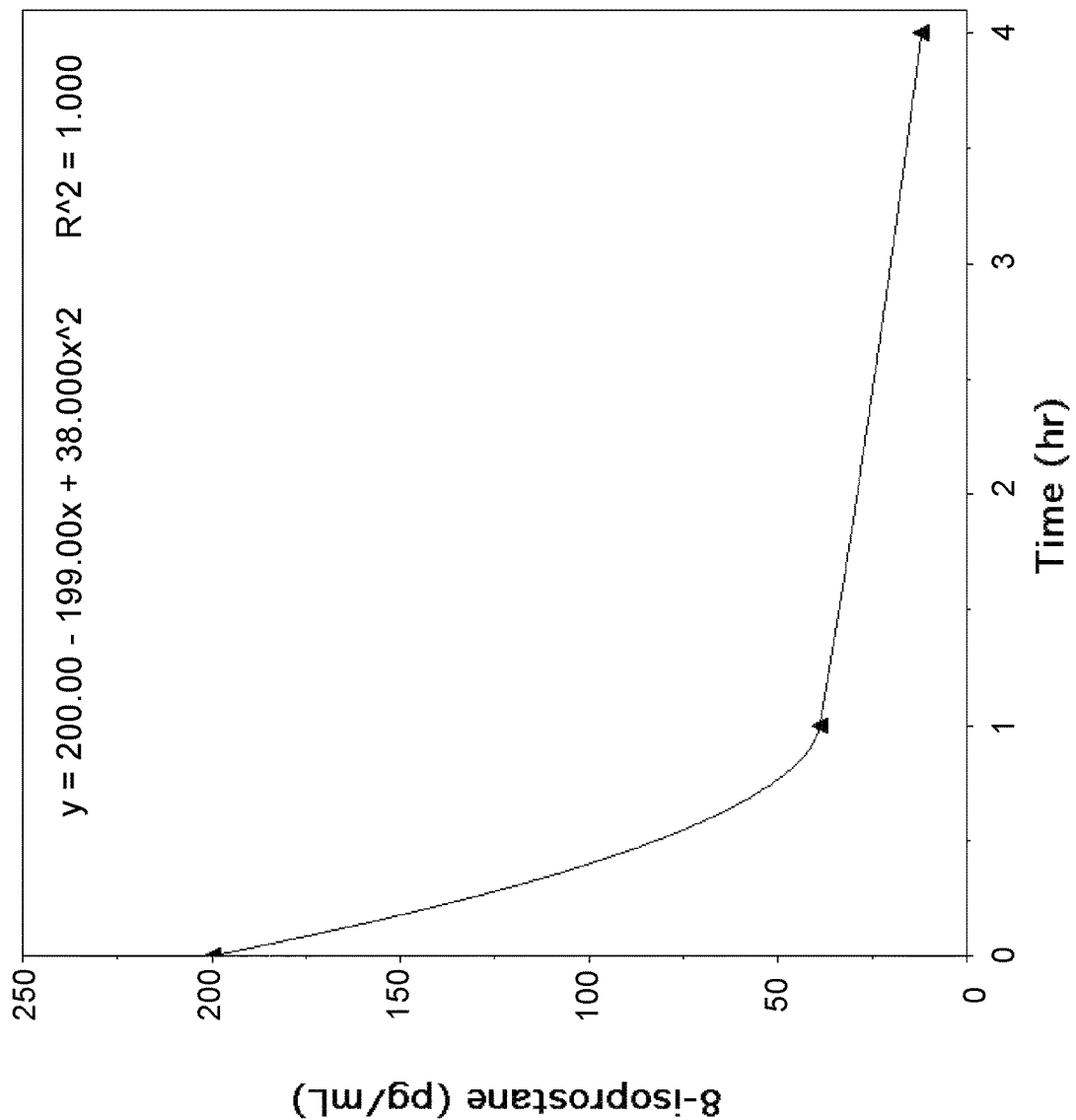
FIG. 7 is a plot of the amount of 8-isoprostane (8-iso PGF2α) in a sample of blood as a function of time following contact with synthetic bimodal carbon particles comprising a microporous/mesoporous modality as described herein.
Figure 8:
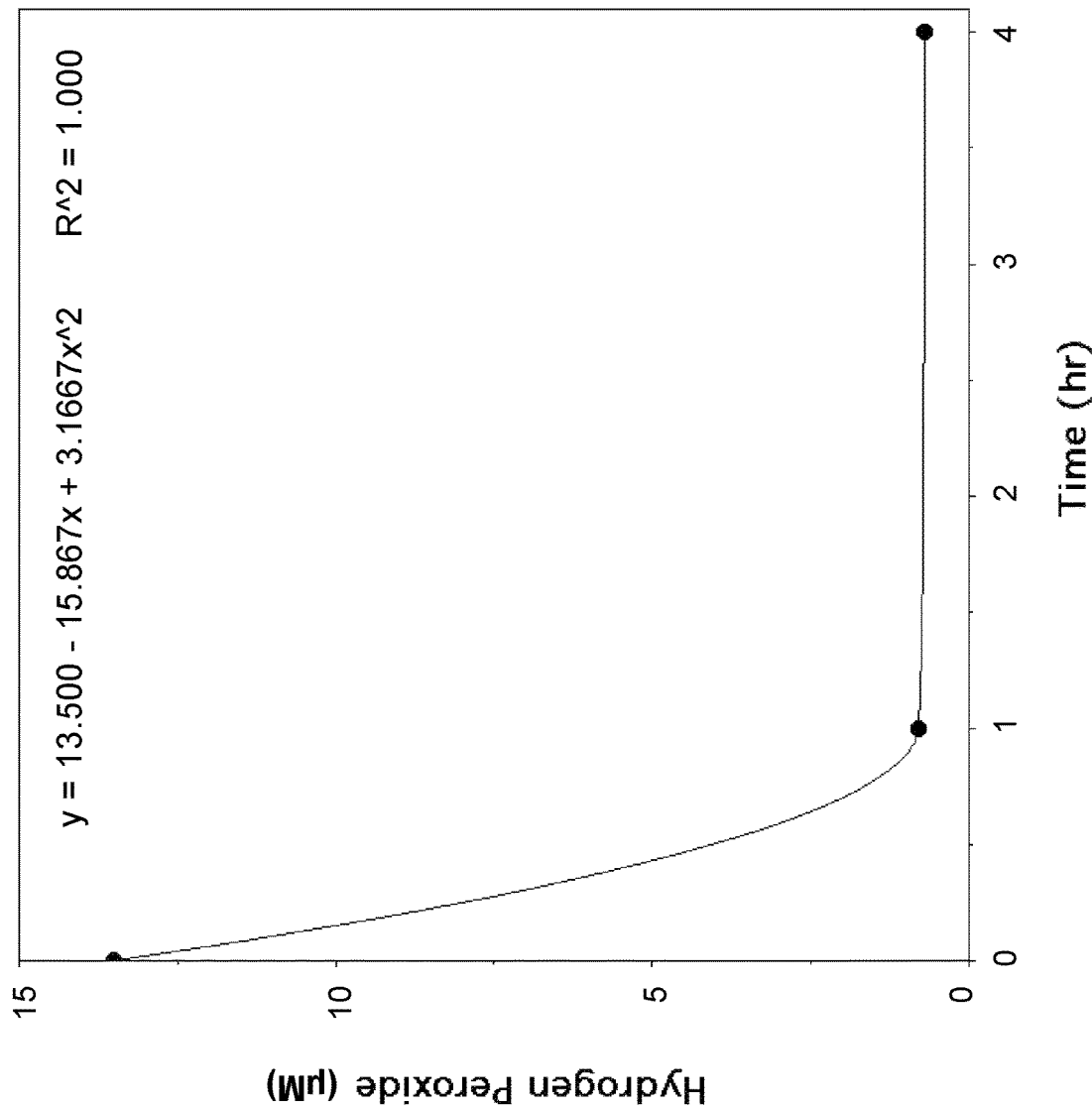
FIG. 8 is a plot of the amount of hydrogen peroxide ($H_2O_2$) in a sample of blood as a function of time following contact with synthetic bimodal carbon particles comprising a microporous/mesoporous modality as described herein.

In an aspect, the SBCP has a macroporous pore size of from about 75 µm to about 1000 µm, alternatively the SBCP has a macroporous size of from about 100 µm to about 750 µm, or alternatively from about 100 µm to about 500 µm. Herein an SBCP suitable for use in the present disclosure may comprise an SBCP having at least two pore size distributions such that the SBCP is a mixture of carbon beads having at least two distributions of macroporous pore sizes. In an aspect, the SBCP may comprise a first population having a macroporous pore size denoted x and a second population having a macroporous pore size y where the SBCP provides a mixture having a ratio of x/y of about 1; alternatively about 5, alternatively about 10, alternatively about 20; alternatively about 50, or alternatively about 100. In some aspects, the SBCP comprises a mixture of two populations wherein the pore size of the first population is approximately twice the pore size of the second population. In some aspects, the SBCP comprises a mixture of three populations where the pore size of a first population is approximately twice the pore size of the second population and the pore size of the third population is approximately two and a half times the pore size of the second population. FIG. 4 depicts aspects of a multimodal modal SBCP of the type disclosed herein with sorbing potency towards preeclamptic disease mediators.

In any of the aforementioned aspects, any of the components of the therapeutic formulation (e.g., resin associated with an affinity ligand and/or the SBCP) may be functionalized with one or more moieties to selectively enhance the affinity of the material for molecules to be removed from the whole blood or plasma. In an aspect of the present disclosure, molecules (e.g., antibodies raised against sEng, anti-antibodies, anti-cytokines and the like, and or synthetic ligands) may be chemically associated with one or more of the therapeutic formulation components via a chemical reaction to link said molecule with the therapeutic formulation component. For example, such molecules may be attached to a polyvinylamine/polysulfone composite hollow-fiber or membrane via a Schiff reaction-based on a glutaraldehyde cross-linking method. In an alternative aspect of the present disclosure, one or molecules of interest may be aldehyde activated by an oxidizing agent (e.g., sodium meta-periodate) to generate functional moieties capable of reacting with (e.g., binding) one or more molecules of interest. An example of this type of reaction is schematized below:

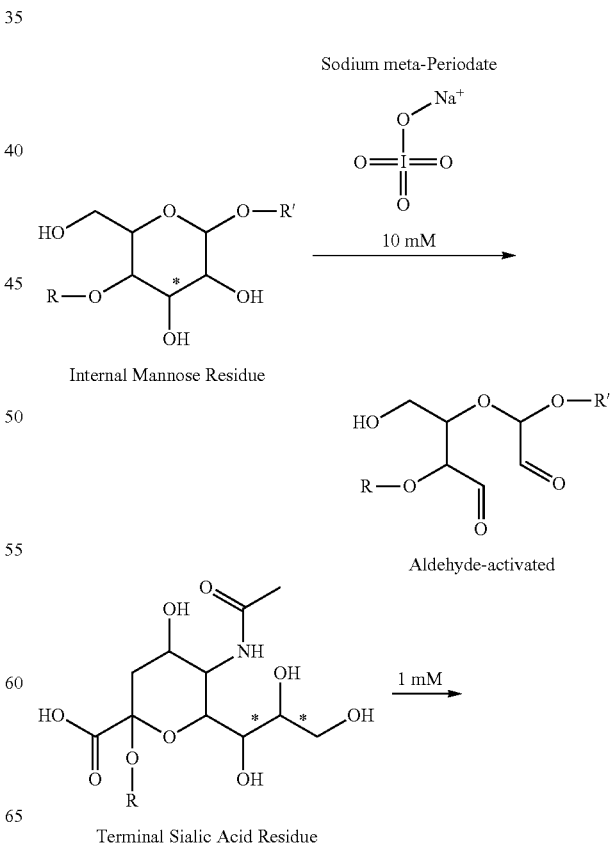

-continued

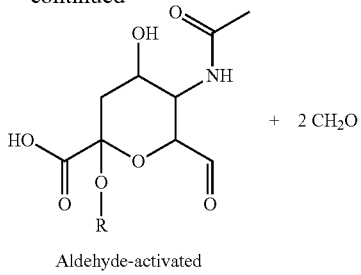

+ 2 CH$_2$O

Aldehyde-activated

It is contemplated that other methodologies for functionalization of the materials disclosed herein may be carried out in order to improve the efficiency with which the therapeutic formulation removes one or more molecules and/or to alter the therapeutic formulation for use in particular applications.

Schemes 1-3 depict aspects of methods for functionalizing components of the therapeutic formulation as disclosed herein. The resultant materials are depicted in FIG. 3.

Scheme 1 represents a schematic representation of covalent immobilization of anti-sFlt-1 Ab to polyvinyl alcohol beads ("PVA") treated with sodium periodate (NaIO$_4$). Difference quenching can provide electronegative (i.e., lysine pI 9.6) or electropositive (i.e., cysteine pI 5.2) charges to the resulting affinity resin. Scheme 1 (scheme proceeds from left to right and when the scheme presents an arrow with no text to the right of the arrow, the scheme continues on the portion of the page(s) that follow directly after said arrow):

Scheme 1

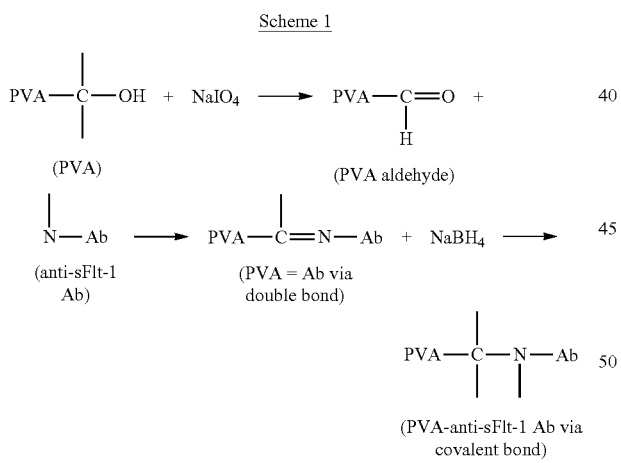

Scheme 2 represents a schematic representation of covalent immobilization of anti-sEndoglin Ab to polyvinyl alcohol beads ("PVA") treated with sodium periodate (NaIO$_4$). Different quenching can provide electronegative (i.e., lysine pI 9.6) or electropositive (i.e., cysteine pI 5.2) charges to the resulting affinity resin. Scheme 2 (scheme proceeds from left to right and when the scheme presents an arrow with no text to the right of the arrow, the scheme continues on the portion of the page(s) that follow directly after said arrow):

Scheme 2

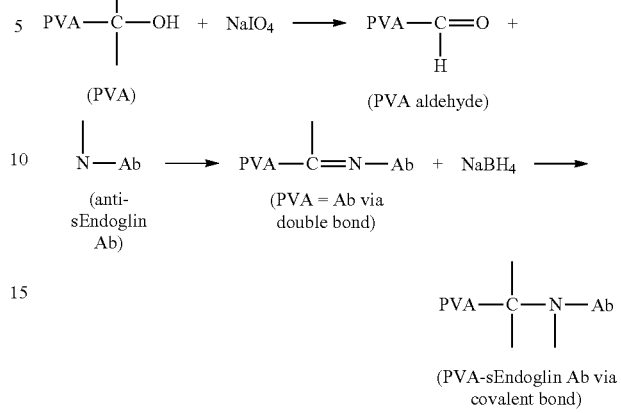

Scheme 3 represents a schematic representation of polyvinyl alcohol beads ("PVA") polymerization reaction in order to covalently link several beads together. Scheme 3 (scheme proceeds from left to right and when the scheme presents an arrow with no text to the right of the arrow, the scheme continues on the portion of the page(s) that follow directly after said arrow):

Scheme 3

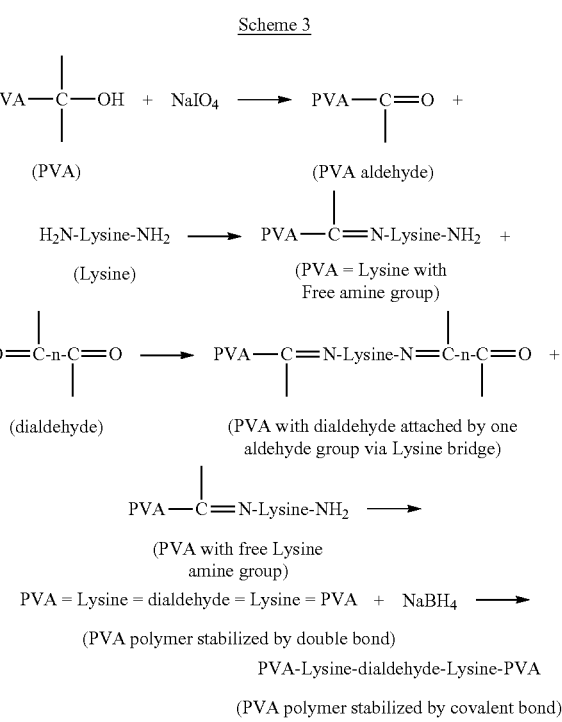

or alternatively:

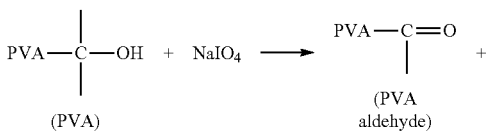

-continued

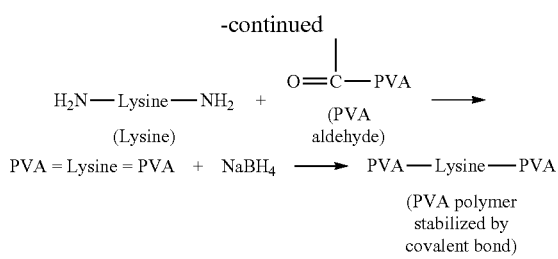

In an aspect, any or all of the therapeutic formulation components may be subjected to a sanitization process prior contacting whole blood or plasma. Herein, the sanitization process refers to a method of treating the therapeutic formulation components in order to (i) remove pathogens; (ii) reduce the amount of fine particulates and leachables; (iii) reduce the amount of trapped air and (iv) sterilize the materials. Therapeutic formulation components that have been subjected to the sanitization process disclosed herein are considered to have been converted from an industrial grade material to a pharmaceutical grade material with a concomitant increase in hemocompatability.

In an aspect, a method for sanitization of the therapeutic formulation components comprises a dry heat treatment. Dry heat treatment of the therapeutic formulation components may be carried out at a temperature equal to or greater than about 180° C. for a time period equal to or greater than about 4 hours, alternatively at a temperature of equal to or greater than about 200° C. for a time period of equal to or greater than about 1 hour, or alternatively at a temperature of 250° C. for a time period of equal to or greater than about 30 min. Dry heat treatment of the therapeutic formulation components may function to reduce the bioburden of the material and particularly the amount of pathogenic (e.g., bacteria, viruses, fungi, etc.) and pyrogenic (e.g., endotoxin) substances associated with the therapeutic formulation components. For example, the total amount of pathogenic substances associated with the heat-treated therapeutic formulation components may be reduced by greater than about 50%, alternatively greater than about 90%, alternatively greater than about 91%, alternatively greater than about 92%, alternatively greater than about 93%, alternatively greater than about 94%, alternatively greater than about 95%, alternatively greater than about 96%, alternatively greater than about 97%, alternatively greater than about 98%, alternatively greater than about 99%, or alternatively about 100% when compared to the amount present in the therapeutic formulation components prior to heat treatment.

In an aspect, the bioburden of the therapeutic formulation components is reduced by about 100% through the use of a dry heat treatment. Alternatively, the bioburden of the therapeutic formulation components is reduced through the use of any suitable methodology compatible with the therapeutic formulation components and the other aspects of the present disclosure. In some aspects, the bioburden of the therapeutic formulation components is reduced by 100% utilizing methodologies consistent with jurisdictional guidelines for the sanitization of materials that will contact mammalian blood and produce a product that will be subsequently utilized in mammals.

In an aspect, a method for sanitization further comprises the removal of fine particulates and leachables from the heat-treated therapeutic formulation components. Herein, particulates smaller than about 30 microns are referred to as "fines" while "leachables" describe the organic compounds that can be eluted from the therapeutic formulation in the presence/absence of an applied sample. In an aspect, removal of the fine particulates and leachables from the heat-treated therapeutic formulation components comprises contacting the heat-treated therapeutic formulation components with water, removing water from the heat-treated therapeutic formulation components to produce a washed therapeutic formulation components, contacting the washed therapeutic formulation components with a salt solution to produce a modified therapeutic formulation components, and removing the salt solution from the modified therapeutic formulation components to produce a processed therapeutic formulation components. The heat-treated therapeutic formulation components may be contacted with from about 4 volumes to about 10 volumes of water, alternatively from about 5 volumes to about 10 volumes of water or alternatively from about 6 volumes to about 8 volumes of water. Contacting of the therapeutic formulation components with a substance may be carried out in any suitable vessel. For example, the therapeutic formulation components may be positioned within a cartridge or column to facilitate contacting with one or more substances of the type disclosed herein. For example, the washed therapeutic formulation components may be contacted with a solution comprising sodium chloride salt at a concentration of 3 g/dL. The washed therapeutic formulation components may be contacted with from about 4 volumes to about 10 volumes of salt solution based on the total volume of the therapeutic formulation components, alternatively from about 6 volumes to about 10 volumes of salt solution or alternatively from about 6 volumes to about 8 volumes of salt solution. It is contemplated that other salt solutions providing similar pH and osmolarity, such as known to the ordinarily skilled artisan and compatible with the other methods and compositions of the present disclosure, may be employed to facilitate the removal of fine particulates and leachables from the therapeutic formulation components.

For either the removal of water to produce a washed therapeutic formulation components or the removal of salt to produce a processed therapeutic formulation components, the removal may be effected using any suitable methodology. For example, the removal of fine particulates and leachables may be carried out by placing the therapeutic formulation components in a column which may be allowed to drain under gravity until no further filtrate is detected. In some aspects, the therapeutic formulation components may be subjected to a plurality of processes for the removal of fine particulates and leachables. Further, in some aspects, the solution produced by contacting the therapeutic formulation components with water and/or a salt solution may be analyzed to determine the amount of fine particulates and/or leachables removed following contact. Such determinations may be made and the process for removal of fine particulates and/or leachables repeated until some user and/or process desired level of fine particulates and/or leachables is achieved.

In an aspect, a method for sanitization further comprises dewatering the processed therapeutic formulation components. Water present with the therapeutic formulation components has the tendency to separate from the material resulting in compaction and a reduction in flow properties. De-watering is the process of removing extraneous fluid (typically water or aqueous solutions) from wet or slurried particles without removing fluid in the particles (i.e., prevent evaporative drying of the particles). Herein, "extraneous" means any fluid outside the particles. Therefore any fluid absorbed into the polymer matrix or present in the pores is not considered extraneous.

Any suitable methodology may be employed for the dewatering of the processed therapeutic formulation components. Examples of methodologies suitable for use in dewatering the processed therapeutic formulation components include without limitation the passage of air through the particles. The resultant material is referred to as the dewatered therapeutic formulation components. In an aspect, dewatering of the processed therapeutic formulation components is carried out using a dewatering apparatus.

In an aspect, a method for sanitization further comprises aseptic processing of the dewatered therapeutic formulation components, also referred to as sterile fill and sterilization to produce sanitized therapeutic formulation components. Sterility may be achieved using any suitable methodology. For example, sterile processing may include the use of clean rooms, bacteria-retaining filters, and dry or steam heat. In an aspect, aseptic processing of the dewatered therapeutic formulation components comprises terminal sterilization by autoclaving (e.g., at 121° C., 15 psi for 30 min), gas sterilization, e-beam sterilization, gamma radiation, or combinations thereof.

In an aspect, any of the therapeutic formulation components may be contacted with a compatibilizer which functions to coat at least a portion of the surface area of the therapeutic formulation components. Herein, a compatibilizer refers to a substance that functions to increase the biocompatibility of the therapeutic formulation components with biological fluids (e.g., plasma) and may aid in decreasing the binding of non-target molecules to the therapeutic formulation components. In an aspect, the compatibilizer comprises a polysaccharide, a glucan, albumin, mannitol, a starch, or combinations thereof.

In an aspect, the compatibilizer comprises dextran. Dextrans, representations are depicted in Formula I, are polysaccharides having a linear backbone of α-linked D-glucopyranosyl repeating units. In an aspect, a dextran suitable for use in the present disclosure has an average molecular weight ranging from about 1 kDa to about 500 kDa, alternatively from about 1 kDa to about 70 kDa, alternatively from about 1 kDa to about 40 kDa, or alternatively from about 40 kDa to about 70 kDa. Nonlimiting examples of compatibilizers suitable for use in the present disclosure include DEXTRAN-1, DEXTRAN-40 and DEXTRAN-70 commercially available from Hospira Inc.

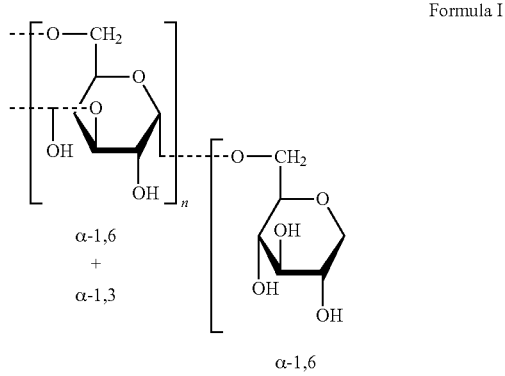

Formula I

In an aspect, the compatibilizer comprises hydroxyethyl starch. Hydroxyethyl starch, depicted in Formula II, is a nonionic starch derivative that is commonly used as a volume expander in a type of intravenous therapy that has the function of providing volume for the circulatory system.

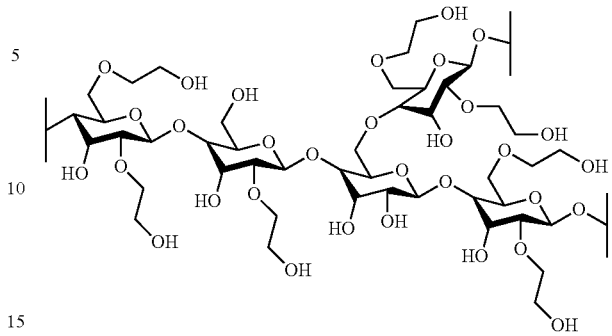

Formula II

In an aspect, the compatiblizer comprises a mixture of albumin and mannitol. Serum albumin is the main protein of human blood plasma whose primary function is to regulate the colloidal osmotic pressure of blood. Mannitol, (2R,3R, 4R,5R)-Hexan-1,2,3,4,5,6-hexol, is a sugar alcohol, which can function an Osmotic Diuretic. The weight ratio of albumin to mannitol in the compatibilizer may range from 20:1 to 1:1, alternatively from 18:1 to 1:1, or alternatively from 15:1 to 10:1.

Without wishing to be limited by theory, the compatibilizer (e.g., dextran) may function to prime the device (i.e., apparatus having columns containing the therapeutic formulation) and may lessen complications by blocking the initial exposure of blood components and plasma to foreign surfaces while maintaining a higher level of colloid osmotic pressure. In an aspect, the compatibilizer is dextran 40 which may function in (i) preventing shear-induced fines formation via a lubrication effect; (ii) serving as a priming agent to prevent activation of plasma and other blood components following early primary exposure; and (iii) modulating sorbing capacity of porous sorbents such as synthetic microporous/mesoporous carbon. For example, the therapeutic formulation components packed into columns as components of an apparatus of the type disclosed herein, during storage/distribution can be exposed to relatively high shear stresses which can be a continuous source of particulates while dextran may prevent fines formation by lubrication at any shear condition.

Therapeutic formulation components suitable for use in the present disclosure may be contacted with the compatibilizer using any suitable methodology. In an aspect, the compatibilizer is dextran which may be formulated as a solution suitable for use in the present disclosure having from about 1 weight percent (wt. %) dextran about 10 wt. % dextran, alternatively from about 2 wt. % to about 9 wt. % or alternatively from about 3 wt. % to about 7 wt. %. In an aspect, the compatibilizer is hydroxyethyl starch which may be formulated as a solution suitable for use in the present disclosure having from about 1 wt. % to about 6 wt. % hydroxyethyl starch, alternatively from about 1.5 wt. % to about 6 wt. % hydroxyethyl starch or alternatively from about 2 wt. % to about 6 wt. % hydroxyethyl starch. The resultant compatibilized therapeutic formulation components may be characterized by the formation of a coating of the compatibilizer on the particles of the therapeutic formulation components such that the coating covers greater than about 50% of the particle's surface; alternatively, greater than about 60%, 70%, 80% or 90% of the particle's surface.

In an aspect, the components of the therapeutic formulation are present in any amount suitable to effectively reduce the amount of preeclamptic mediators in a plasma or blood sample. For example a therapeutic formulation may comprise (i) a PVA resin bead with affinity ligands directed toward the syncytiotrophoblast-derived factor sFIT; (ii) a PVA resin bead with affinity ligands directed toward the syncytiotrophoblast-derived factor sEng; and (iii) a synthetic carbon particle, all of the type disclosed herein. Such a therapeutic formulation is designated therapeutic formulation X, TFX. In TFX the ratio of (i):(ii):(iii) may range from 1:1000:1000 to 1000:1:1, alternatively from 10:100: 500 to 500:100:10, alternatively from 100:10:500 to 500: 10:100, alternatively from 0.1:1:10 to 10:1:0.1: or alternatively from 1:1:1.

In an aspect, a sample (e.g., whole blood or plasma) is contacted with a therapeutic formulation of the type disclosed herein (e.g., TFX) that is a component of an extracorporeal device.

Figure 2:
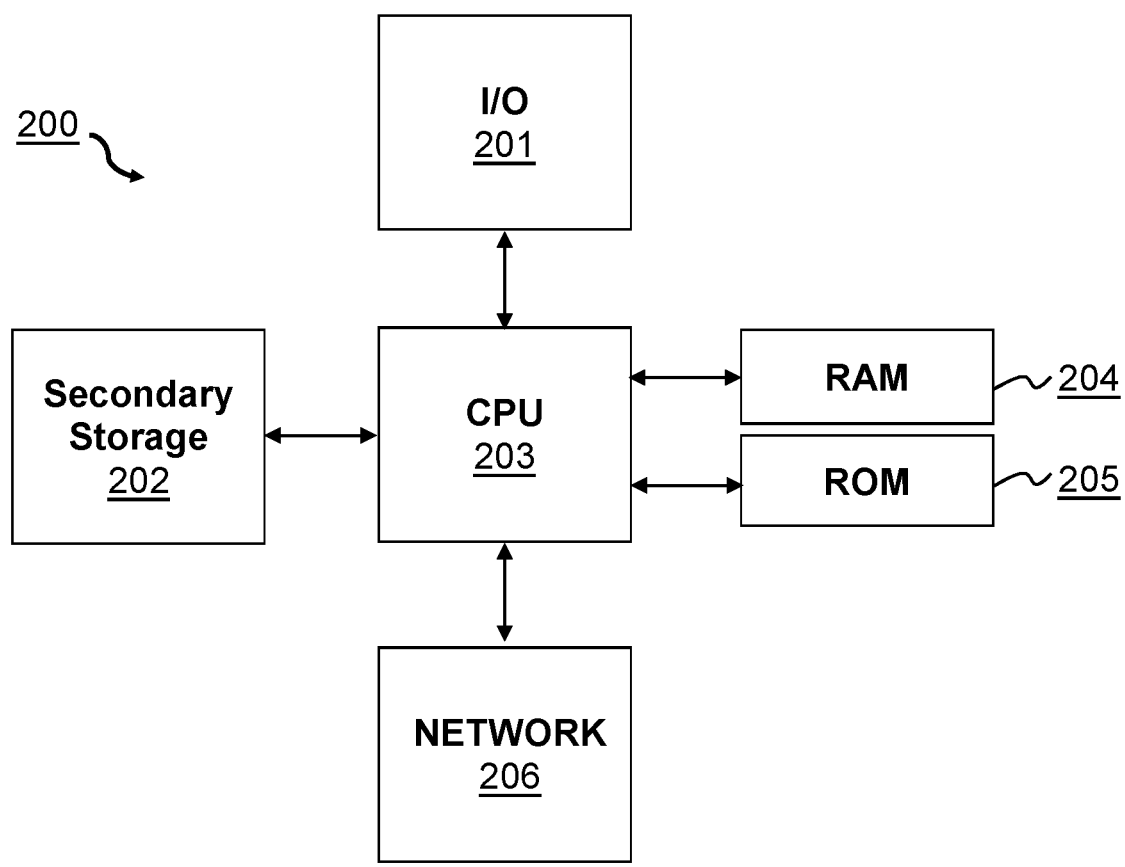
FIG. 2 depicts aspects of a computer system as disclosed herein.

Any aspect of the present disclosure may be carried out manually. In the alternative, one or more aspects disclosed herein may be automated. FIG. 2 illustrates a computer system 200 suitable for implementing one or more aspects disclosed herein. The computer system 200 includes a processor 203 (which may be referred to as a central processor unit or CPU) that is in communication with memory devices including secondary storage 202, read only memory (ROM) 205, random access memory (RAM) 204, input/output (I/O) devices 201, and network connectivity devices 206. The processor 203 may be implemented as one or more CPU chips.

It is understood that by programming and/or loading executable instructions onto the computer system 200, at least one of the CPU 203, the RAM 204, and the ROM 205 are changed, transforming the computer system 200 in part into a particular machine or apparatus having the novel functionality taught by the present disclosure. It is fundamental to the electrical engineering and software engineering arts that functionality that can be implemented by loading executable software into a computer can be converted to a hardware implementation by well-known design rules. Decisions between implementing a concept in software versus hardware typically hinge on considerations of stability of the design and numbers of units to be produced rather than any issues involved in translating from the software domain to the hardware domain. Generally, a design that is still subject to frequent change may be preferred to be implemented in software, because re-spinning a hardware implementation is more expensive than re-spinning a software design. Generally, a design that is stable that will be produced in large volume may be preferred to be implemented in hardware, for example in an application specific integrated circuit (ASIC), because for large production runs the hardware implementation may be less expensive than the software implementation. Often a design may be developed and tested in a software form and later transformed, by well-known design rules, to an equivalent hardware implementation in an application specific integrated circuit that hardwires the instructions of the software. In the same manner as a machine controlled by a new ASIC is a particular machine or apparatus, likewise a computer that has been programmed and/or loaded with executable instructions may be viewed as a particular machine or apparatus.

The secondary storage 202 is typically comprised of one or more disk drives or tape drives and is used for non-volatile storage of data and as an over-flow data storage device if RAM 204 is not large enough to hold all working data. Secondary storage 202 may be used to store programs which are loaded into RAM 204 when such programs are selected for execution. The ROM 205 is used to store instructions and perhaps data which are read during program execution. ROM 205 is a non-volatile memory device which typically has a small memory capacity relative to the larger memory capacity of secondary storage 202. The RAM 204 is used to store volatile data and perhaps to store instructions. Access to both ROM 205 and RAM 204 is typically faster than to secondary storage 202. The secondary storage 202, the RAM 204, and/or the ROM 205 may be referred to in some contexts as computer readable storage media and/or non-transitory computer readable media.

I/O devices 201 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 206 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), long-term evolution (LTE), worldwide interoperability for microwave access (WiMAX), and/or other air interface protocol radio transceiver cards, and other well-known network devices. These network connectivity devices 206 may enable the processor 203 to communicate with an Internet or one or more intranets. With such a network connection, it is contemplated that the processor 203 might receive information from the network, or might output information to the network in the course of performing the above-described method steps. Such information, which is often represented as a sequence of instructions to be executed using processor 203, may be received from and outputted to the network, for example, in the form of a computer data signal embodied in a carrier wave.

Such information, which may include data or instructions to be executed using processor 203 for example, may be received from and outputted to the network, for example, in the form of a computer data baseband signal or signal embodied in a carrier wave. The baseband signal or signal embodied in the carrier wave generated by the network connectivity devices 206 may propagate in or on the surface of electrical conductors, in coaxial cables, in waveguides, in an optical conduit, for example an optical fiber, or in the air or free space. The information contained in the baseband signal or signal embedded in the carrier wave may be ordered according to different sequences, as may be desirable for either processing or generating the information or transmitting or receiving the information. The baseband signal or signal embedded in the carrier wave, or other types of signals currently used or hereafter developed, may be generated according to several methods well known to one skilled in the art. The baseband signal and/or signal embedded in the carrier wave may be referred to in some contexts as a transitory signal.

The processor 203 executes instructions, codes, computer programs, scripts which it accesses from hard disk, floppy disk, optical disk (these various disk based systems may all be considered secondary storage 202), ROM 205, RAM 204, or the network connectivity devices 206. While only one processor 203 is shown, multiple processors may be present. Thus, while instructions may be discussed as executed by a processor, the instructions may be executed simultaneously, serially, or otherwise executed by one or multiple processors. Instructions, codes, computer programs, scripts, and/or data that may be accessed from the secondary storage 202, for example, hard drives, floppy disks, optical disks, and/or other device, the ROM 205, and/or the RAM 204 may be referred to in some contexts as non-transitory instructions and/or non-transitory information.

In an aspect, the computer system 200 may comprise two or more computers in communication with each other that collaborate to perform a task. For example, but not by way of limitation, an application may be partitioned in such a way as to permit concurrent and/or parallel processing of the instructions of the application. Alternatively, the data processed by the application may be partitioned in such a way as to permit concurrent and/or parallel processing of different portions of a data set by the two or more computers. In an aspect, virtualization software may be employed by the computer system 200 to provide the functionality of a number of servers that is not directly bound to the number of computers in the computer system 200. For example, virtualization software may provide twenty virtual servers on four physical computers. In an aspect, the functionality disclosed above may be provided by executing the application and/or applications in a cloud computing environment. Cloud computing may comprise providing computing services via a network connection using dynamically scalable computing resources. Cloud computing may be supported, at least in part, by virtualization software. A cloud computing environment may be established by an enterprise and/or may be hired on an as-needed basis from a third party provider. Some cloud computing environments may comprise cloud computing resources owned and operated by the enterprise as well as cloud computing resources hired and/or leased from a third party provider.

In an aspect, some or all of the functionality disclosed above may be provided as a computer program product. The computer program product may comprise one or more computer readable storage medium having computer usable program code embodied therein to implement the functionality disclosed above. The computer program product may comprise data structures, executable instructions, and other computer usable program code. The computer program product may be embodied in removable computer storage media and/or non-removable computer storage media. The removable computer readable storage medium may comprise, without limitation, a paper tape, a magnetic tape, magnetic disk, an optical disk, a solid state memory chip, for example analog magnetic tape, compact disk read only memory (CD-ROM) disks, floppy disks, jump drives, digital cards, multimedia cards, and others. The computer program product may be suitable for loading, by the computer system 200, at least portions of the contents of the computer program product to the secondary storage 202, to the ROM 205, to the RAM 204, and/or to other non-volatile memory and volatile memory of the computer system 200. The processor 203 may process the executable instructions and/or data structures in part by directly accessing the computer program product, for example by reading from a CD-ROM disk inserted into a disk drive peripheral of the computer system 200. Alternatively, the processor 203 may process the executable instructions and/or data structures by remotely accessing the computer program product, for example by downloading the executable instructions and/or data structures from a remote server through the network connectivity devices 206. The computer program product may comprise instructions that promote the loading and/or copying of data, data structures, files, and/or executable instructions to the secondary storage 202, to the ROM 205, to the RAM 204, and/or to other non-volatile memory and volatile memory of the computer system 200.

In some contexts, a baseband signal and/or a signal embodied in a carrier wave may be referred to as a transitory signal. In some contexts, the secondary storage 202, the ROM 205, and the RAM 204 may be referred to as a non-transitory computer readable medium or a computer readable storage media. A dynamic RAM aspect of the RAM 204, likewise, may be referred to as a non-transitory computer readable medium in that while the dynamic RAM receives electrical power and is operated in accordance with its design, for example during a period of time during which the computer 200 is turned on and operational, the dynamic RAM stores information that is written to it. Similarly, the processor 203 may comprise an internal RAM, an internal ROM, a cache memory, and/or other internal non-transitory storage blocks, sections, or components that may be referred to in some contexts as non-transitory computer readable media or computer readable storage media.

In an aspect, the compositions and methods disclosed herein are utilized in the treatment of one or more adverse conditions associated with pregnancy. In an aspect, the medical condition is selected from the group consisting of preeclampsia, toxemia, and eclampsia.

In any aspect wherein the compositions and methodologies are utilized in the treatment of a medical condition such as preeclampsia or a related disorder. In an aspect, a component of the therapeutic formulation is a resin bead with affinity ligands directed toward the syncytiotrophoblast-derived factor, other treatments (e.g., conventional therapies) may be utilized in conjunction with the disclosed subject matter. For example, a method of the present disclosure comprises subjecting a patient experiencing preeclampsia to an extracorporeal therapy comprising the compositions, devices and methodologies disclosed herein. Such subjects may additionally be administered one or more active agents, in a therapeutically effective amount, as a component of a conventional therapy to ameliorate one or more symptoms of the preeclampic or related condition or unrelated condition. Examples of additional active agents include but are not limited to: (a) antimicrobials, (b) steroids; (c) pain medications (e.g., aspirin, an NSAID, and a local anesthetic); (d) anti-inflammatory agents; (e) hormones; and (f) combinations thereof. Such additional active agents may also be present in a therapeutically effective amount.

Examples of additional active agents that may be administered to a subject undergoing methodologies of the type disclosed herein include, but are not limited to, anesthetics, hypnotics, sedatives and sleep inducers, antipsychotics, antidepressants, antiallergics, antianginals, antiarthritics, antiasthmatics, antidiabetics, antidiarrheal drugs, anticonvulsants, antigout drugs, antihistamines, antipruritics, emetics, antiemetics, antispasmodics, appetite suppressants, neuroactive substances, neurotransmitter agonists, antagonists, receptor blockers and reuptake modulators, beta-adrenergic blockers, calcium channel blockers, disulfuram and disulfuram-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, antitussives, histamine-blocking drugs, monoamine oxidase inhibitor.

Specific compounds that may be administered to a subject undergoing methodologies of the type disclosed herein include silver sulfadiazine, Nystatin, Nystatin/triamcinolone, Bacitracin, nitrofurazone, nitrofurantoin, a polymyxin (e.g., Colistin, Surfactin, Polymyxin E, and Polymyxin B), doxycycline, antimicrobial peptides (e.g., natural and synthetic origin), NEOSPORIN® (i.e., Bacitracin, Polymyxin B, and Neomycin), POLYSPORIN® (i.e., Bacitracin and Polymyxin B). Additional antimicrobials include topical antimicrobials (i.e., antiseptics), examples of which include silver salts, iodine, benzalkonium chloride, alcohol, hydrogen peroxide, chlorhexidine, acetaminophen; Alfentanil Hydrochloride; Aminobenzoate Potassium; Aminobenzoate Sodium; Anidoxime; Anileridine; Anileridine Hydrochloride; Anilopam Hydrochloride; Anirolac; Antipyrine; Aspirin; Benoxaprofen; Benzydamine Hydrochloride; Bicifadine Hydrochloride; Brifentanil Hydrochloride; Bromadoline Maleate; Bromfenac Sodium; Buprenorphine Hydrochloride; Butacetin; Butixirate; Butorphanol; Butorphanol Tartrate; Carbamazepine; Carbaspirin Calcium; Carbiphene Hydrochloride; Carfentanil Citrate; Ciprefadol Succinate; Ciramadol; Ciramadol Hydrochloride; Clonixeril; Clonixin; Codeine; Codeine Phosphate; Codeine Sulfate; Conorphone Hydrochloride; Cyclazocine; Dexoxadrol Hydrochloride; Dexpemedolac; Dezocine; Diflunisal; Dihydrocodeine Bitartrate; Dimefadane; Dipyrone; Doxpicomine Hydrochloride; Drinidene; Enadoline Hydrochloride; Epirizole; Ergotamine Tartrate; Ethoxazene Hydrochloride; Etofenamate; Eugenol; Fenoprofen; Fenoprofen Calcium; Fentanyl Citrate; Floctafenine; Flufenisal; Flunixin; Flunixin Meglumine; Flupirtine Maleate; Fluproquazone; Fluradoline Hydrochloride; Flurbiprofen; Hydromorphone Hydrochloride; Ibufenac; Indoprofen; Ketazocine; Ketorfanol; Ketorolac Tromethamine; Letimide Hydrochloride; Levomethadyl Acetate; Levomethadyl Acetate Hydrochloride; Levonantradol Hydrochloride; Levorphanol Tartrate; Lofemizole Hydrochloride; Lofentanil Oxalate; Lorcinadol; Lomoxicam; Magnesium Salicylate; Mefenamic Acid; Menabitan Hydrochloride; Meperidine Hydrochloride; Meptazinol Hydrochloride; Methadone Hydrochloride; Methadyl Acetate; Methopholine; Methotrimeprazine; Metkephamid Acetate; Mimbane Hydrochloride; Mirfentanil Hydrochloride; Molinazone; Morphine Sulfate; Moxazocine; Nabitan Hydrochloride; Nalbuphine Hydrochloride; Nalmexone Hydrochloride; Namoxyrate; Nantradol Hydrochloride; Naproxen; Naproxen Sodium; Naproxol; Nefopam Hydrochloride; Nexeridine Hydrochloride; Noracymethadol Hydrochloride; Ocfentanil Hydrochloride; Octazamide; Olvanil; Oxetorone Fumarate; Oxycodone; Oxycodone Hydrochloride; Oxycodone Terephthalate; Oxymorphone Hydrochloride; Pemedolac; Pentamorphone; Pentazocine; Pentazocine Hydrochloride; Pentazocine Lactate; Phenazopyridine Hydrochloride; Phenyramidol Hydrochloride; Picenadol Hydrochloride; Pinadoline; Pirfenidone; Piroxicam Olamine; Pravadoline Maleate; Prodilidine Hydrochloride; Profadol Hydrochloride; Propiram Fumarate; Propoxyphene Hydrochloride; Propoxyphene Napsylate; Proxazole; Proxazole Citrate; Proxorphan Tartrate; Pyrroliphene Hydrochloride; Remifentanil Hydrochloride; Salcolex; Salethamide Maleate; Salicylamide; Salicylate Meglumine; Salsalate; Sodium Salicylate; Spiradoline Mesylate; Sufentanil; Sufentanil Citrate; Talmetacin; Talniflumate; Talosalate; Tazadolene Succinate; Tebufelone; Tetrydamine; Tifurac Sodium; Tilidine Hydrochloride; Tiopinac; Tonazocine Mesylate; Tramadol Hydrochloride; Trefentanil Hydrochloride; Trolamine; Veradoline Hydrochloride; Verilopam Hydrochloride; Volazocine; Xorphanol Mesylate; Xylazine Hydrochloride; Zenazocine Mesylate; Zomepirac Sodium; Zucapsaicin, Aflyzosin Hydrochloride; Alipamide; Althiazide; Amiquinsin Hydrochloride; Amlodipine Besylate; Amlodipine Maleate; Anaritide Acetate; Atiprosin Maleate; Belfosdil; Bemitradine; Bendacalol Mesylate; Bendroflumethiazide; Benzthiazide; Betaxolol Hydrochloride; Bethanidine Sulfate; Bevantolol Hydrochloride; Biclodil Hydrochloride; Bisoprolol; Bisoprolol Fumarate; Bucindolol Hydrochloride; Bupicomide; Buthiazide: Candoxatril; Candoxatrilat; Captopril; Carvedilol; Ceronapril; Chlorothiazide Sodium; Cicletanine; Cilazapril; Clonidine; Clonidine Hydrochloride; Clopamide; Cyclopenthiazide; Cyclothiazide; Darodipine; Debrisoquin Sulfate; Delapril Hydrochloride; Diapamide; Diazoxide; Dilevalol Hydrochloride; Diltiazem Malate; Ditekiren; Doxazosin Mesylate; Eeadotril; Enalapril Maleate; Enalaprilat; Enalkiren; Endralazine Mesylate; Epithiazide; Eprosartan; Eprosartan Mesylate; Fenoldopam Mesylate; Flavodilol Maleate; Flordipine; Flosequinan; Fosinopril Sodium; Fosinoprilat; Guanabenz; Guanabenz Acetate; Guanacline Sulfate; Guanadrel Sulfate; Guancydine; Guanethidine Monosulfate; Guanethidine Sulfate; Guanfacine Hydrochloride; Guanisoquin Sulfate; Guanoclor Sulfate; Guanoctine Hydrochloride; Guanoxabenz; Guanoxan Sulfate; Guanoxyfen Sulfate; Hydralazine Hydrochloride; Hydralazine Polistirex; Hydroflumethiazide; Indacrinone; Indapamide; Indolaprif Hydrochloride; Indoramin; Indoramin Hydrochloride; Indorenate Hydrochloride; Lacidipine; Leniquinsin; Levcromakalim; Lisinopril; Lofexidine Hydrochloride; Losartan Potassium; Losulazine Hydrochloride; Mebutamate; Mecamylamine Hydrochloride; Medroxalol; Medroxalol Hydrochloride; Methalthiazide; Methyclothiazide; Methyldopa; Methyldopate Hydrochloride; Metipranolol; Metolazone; Metoprolol Fumarate; Metoprolol Succinate; Metyrosine; Minoxidil; Monatepil Maleate; Muzolimine; Nebivolol; Nitrendipine; Ofornine; Pargyline Hydrochloride; Pazoxide; Pelanserin Hydrochloride; Perindopril Erbumine; Phenoxybenzamine Hydrochloride; Pinacidil; Pivopril; Polythiazide; Prazosin Hydrochloride; Primidolol; Prizidilol Hydrochloride; Quinapril Hydrochloride; Quinaprilat; Quinazosin Hydrochloride; Quinelorane Hydrochloride; Quinpirole Hydrochloride; Quinuclium Bromide; Ramipril; Rauwolfia Serpentina; Reserpine; Saprisartan Potassium; Saralasin Acetate; Sodium Nitroprusside; Sulfinalol Hydrochloride; Tasosartan; Teludipine Hydrochloride; Temocapril Hydrochloride; Terazosin Hydrochloride; Terlakiren; Tiamenidine; Tiamenidine Hydrochloride; Tierynafen; Tinabinol; Tiodazosin; Tipentosin Hydrochloride; Trichlormethiazide; Trimazosin Hydrochloride; Trimethaphan Camsylate; Trimoxamine Hydrochloride; Tripamide; Xipamide; Zankiren Hydrochloride; Zofenoprilat Arginine, Alclofenac; Alclometasone Dipropionate; Algestone Acetonide; Alpha Amylase; Ameinafal; Ameinafide; Amfenac Sodium; Amiprilose Hydrochloride; Anakinra; Anirolac; Anitrazafen; Apazone; Balsalazide Di sodium;

Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lornoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Momiflumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; and Zomepirac Sodium.

In an aspect, a method of treating preeclampsia or a related condition comprises subjecting at least a portion of the blood of a subject to an extracorporeal therapy comprising a therapeutic formulation of materials. The therapeutic formulation of materials may be a three component composition where the first component comprises polyvinyl alcohol beads (PVA) with affinity ligands directed toward sFlt-1; the second component comprises polyvinyl alcohol beads (PVA) with affinity ligands directed toward sEng; and the third component comprises SBCP for adsorbing vasoconstrictors, reactive oxygen species and inflammatory cytokines. All PVA and carbon compositions enriched with positively charged beads, e.g., polyamide 6/6 (NYLON) and polyoxymethylene (DELRIN) and/or negatively charged beads, e.g., polyterafloroethylene (TEFLON) or polyamideimide (ToRLoN), in order to reduce non-Newtonian characteristics of whole blood. In such aspects the particle size of the beads may range from about 1 mm to about 12 mm, added to the columns up to 50% by volume, in order to create larger spacing to reduce shear and enhance whole blood flow.

In an aspect, a methodology of the type disclosed herein comprises determining the amount of at least one mediator of preeclampsia in the subject's bodily fluid (e.g., blood). These determinations may be carried out using any suitable methodology and temporally may be carried out before, during, and/or after treating the subject with the disclosed methodologies. In an aspect, the components of the therapeutic formulation may be adjusted to account for the levels of preeclamptic mediators determined to be present in subject's bodily fluids. For example, a subject having elevated levels of preeclamptic mediator may be subjected to extracorporeal treatment with a therapeutic formulation of materials is sufficient to reduce the amount of preeclamptic mediator $\gamma$ to some user-desired level. The amount of each component of the therapeutic formulation of materials may be adjusted to provided individualized therapy based on the type and level of preeclamptic mediators present in a particular subject's bodily fluid (e.g., circulating blood).

In an aspect, the therapeutic formulation comprises at least one preeclamptic mediator-removing material. In some aspects, contacting of at least a portion of the subject's blood with one or more extracorporeal devices comprising the therapeutic formulation of materials results in the removal of at least a portion of the circulating blood preeclamptic mediators. Alternatively, the circulating blood preeclamptic mediators are reduced to an extent sufficient to ameliorate the subject's disease In an aspect, a method of treating a preeclamptic subject comprises subjecting at least a portion of the subject's blood to contact with an extracorporeal device comprising the therapeutic formulation of materials. The subject's blood may be characterized by an initial circulating blood preeclamptic factors level designated x. It is to be understood the subject's blood may be further characterized by the presence of desirable blood components present in an amount a. Subsequent to contact with the extracorporeal device the subject's blood may be characterized by a circulating blood preeclamptic factors level designated y where y is less than x and a level of desirable blood components b where a is about equal to b. For example, y may have a value that is that is from about 10% to about 90% less than x, alternatively from about 20% to about 80% less than x, or alternatively from about 30% to about 70% less than x. In an aspect y has a value that is at least one order of magnitude less than x. In an aspect, b has a value that is ±20% of the value of a, alternatively ±10% the value of a. In an aspect the compositions, methodologies, and systems disclosed herein result in the selective reduction of circulating blood preeclamptic mediators with a concomitant retention of desirable blood components.

EXAMPLES

The subject matter of the present disclosure having been generally described, the following examples are given as particular embodiments of the disclosure and to demonstrate the practice and advantages thereof. It is understood that the examples are given by way of illustration and are not intended to limit the specification or the claims to follow in any manner.

Example One

The removal of preeclamptic mediators using the compositions and methodologies disclosed herein were investigated. These examples were created by testing sorbing potency of microporous/mesoporous SBCP toward TNF-$\alpha$, IL-1$\beta$, IL-4, IL-6, IL-8, IL-17, TGF-b 1, INF-$\gamma$, and gamma globulins, ET-1, TBX2, 8-isoprostane or $H2O2$. The polymerization of PVA and Schiff base conjugation of Lysine residues mimicking anti-sFlt-1 and anti-CD 105 were performed experimentally as presented in Schemes 1-3 above; however conjugation of PVA with anti-sFlt-1 and anti-CD 105 antibodies is yet to be done. However, proposed chemistry and known cross reactivity of proposed antibodies with target antigens provide indirect but enough evidence about functionality of the device.

Prior to testing, the microporous/mesoporous SBCP were treated/coated with a solution containing 1% dextran in 0.9% NaCl, and 3,000 U HMW heparin, and filled with 76 mL of spiked human fresh frozen plasma, warmed to 37° C. Before spiking, human fresh frozen plasma blood was filtered using 20 μm Pall filter, which was disconnected during testing. In the extracorporeal experiment, the backpressure determined the flow rate generated by a peristaltic pump. The sampling occurred at 0, 1, and 4 hours. The experiments were done in duplicates. Human fresh frozen plasma was spiked with inflammatory cytokines: TNF-α, IL-1β, IL-4, IL-6, IL-8, IL-17, TGF-b 1, INF-γ), and gamma globulins (Sigma-Aldrich, St. Louis, MO: containing IgG and IgM), mimicking preeclamptic states. Other samples were spiked with endothelin-1 (ET-1), thromboxane B2 (TBX2), 8-isoprostane (8-iso-PGF2a), or H2O2 as indicated and the results are depicted in FIGS. 5-9.

Cytokines/chemokines (TNF-α, IL-1β, IL-4, IL-6, IL-8, ITINF-γ) were evaluated by the Multi-Analyte Custom ELISArray Kit (CELISA-CMEH0400A, QIAGEN Inc., Valencia, CA). This ELISArray Kits was designed to survey a specific panel of cytokines or chemokines involved in autoimmunity, inflammation, or T-cell biology in cell culture supernatant, serum or plasma. The ELISA was conducted in accordance with the protocol specified by the manufacturer. The ELISA was read using Bio-Rad Microplate ELISA reader (Model 3550-UV, Bio-Rad Laboratories, Hercules, CA) and calculated using Microplate Manager Software Version 2.2 (Bio-Rad Laboratories). Gamma globulin concentrations were established with Piccolo General Chemistry 13 reagent disk and confirmed by radial immunodiffussion. The results, depicted in FIGS. 5-9, demonstrate the compositions disclosed herein effectively cleared all relevant mediators of preeclampsia and related disorders.

Exemplary aspects of the present disclosure include the following non-limiting aspects.

A first aspect is a three-component composition for use in the treatment of preeclampsia and related disorders comprising: a first component comprising a bimodal synthetic carbon particle mixture; a second component comprising a first resin bead with at least one affinity ligand directed toward syncytiotrophoblast-derived factor sEndoglin; and a third component comprising a second resin bead with at least one affinity ligand directed toward syncytiotrophoblast-derived factor soluble Fms-like tyrosine kinase-1.

A second aspect is three-component composition of the first aspect where the components are separated.

A third aspect is the three-component composition of the first aspect or second aspect wherein the bimodal synthetic carbon particle mixture comprises a first carbon particle having pore size x and a second carbon particle having pore size y where y is greater than x.

A fourth aspect is the three-component composition of the third aspect where y is two times x.

A fifth aspect is the three-component composition of the first aspect wherein the first resin bead comprises gelatin, alginate, collagen type I, fibrin glue, polyglycerol sebacate (PGS), polyglycolic acid (PGA), poly-1-lactide (PLA), poly (lactide-co-glycolide) (PLGA), polyvinyl alcohol (PVA), polycaprolactone, poly(N-isopropylacrylamide), polyethylene (PE), sepharose; silica; polyoxymethylene (POM), polypropylene (PP), polyvinylchloride (PVC), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers or combinations thereof.

A sixth aspect is the three-component composition of the first aspect wherein the second resin bead comprises gelatin, alginate, collagen type I, fibrin glue, polyglycerol sebacate (PGS), polyglycolic acid (PGA), poly-1-lactide (PLA), poly (lactide-co-glycolide) (PLGA), polyvinyl alcohol (PVA), polycaprolactone, poly(N-isopropylacrylamide), polyethylene (PE), sepharose; silica; polyoxymethylene (POM), polypropylene (PP), polyvinylchloride (PVC), polyvinylidene chloride (PVDC), polystyrene (PS), polytetrafluoroethylene (PTFE), polyacrylate, poly(methyl methacrylate) (PMMA), polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), polyurethane (PU), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers or combinations thereof.

A seventh aspect is the three-component composition of any of the first through sixth aspects wherein the first resin bead comprises polyvinyl alcohol.

An eighth aspect is the three-component composition of any of the first through seventh aspects wherein the second resin bead comprises polyvinyl alcohol.

A ninth aspect is the three-component composition of any of the first through eighth aspects wherein the first resin bead is functionalized.

A tenth aspect is the three-component composition of any of the first through ninth aspects wherein the second resin bead is functionalized.

An eleventh aspect is the three-component composition of any of the first through tenth aspects wherein the components are sanitized.

A twelfth aspect is the three-component composition of any of the first through eleventh aspects further comprising a compatibilizer.

A thirteenth aspect is the three-component composition of any of the first through twelfth aspects wherein the first resin bead is negatively charged.

A fourteenth aspect is the three-component composition of any of the first through thirteenth aspects wherein the second resin bead is positively charged.

A fifteenth aspect is the three-component composition of any of the first through twelfth aspects wherein the first resin bead is negatively charged and the second resin bead is positively charged.

A sixteenth aspect is the three-component composition of any of the first through fifteenth aspects wherein the resin beads have a particle size of from about 1 mm to about 12 mm.

A seventeenth aspect is a method comprising contacting a bodily fluid with the three-component composition of any of the first through sixteenth aspects.

An eighteenth aspect is the method of the seventeenth aspect wherein the bodily fluid is obtained from a subject experiencing; (i) a second trimester of a pregnancy; (ii) a systolic blood pressure greater than 140-160 mm Hg wherein the subject is normortensive; (iii) a diastolic blood pressure greater than 90-110 mm Hg on 2 occasions at least 6 hours apart wherein the subject has been resting; (iv) the amount of protein in a urine sample of the subject of equal to or greater than about 300 mg/24 hour collection; or (iv) combinations thereof.

A nineteenth aspect is the method of the seventeenth aspect or the eighteenth aspect wherein contacting occurs in an extracorporeal apparatus having a first column, a second column, and a third column.

A twentieth aspect is the method of the nineteenth aspect wherein the first component is disposed within the first column, the second component is disposed within the second column, and the third component is disposed within the third column.

A twenty-first aspect is the method of the nineteenth aspect or the twentieth aspect where there is fluid communication between the first and second column.

A twenty-second aspect is the method of any of the nineteenth aspect through the twenty-first aspect where there is fluid communication between the second and third column.

A twenty-third aspect is the method of any of the seventeenth aspect through the twenty-second aspect wherein the bodily fluid comprises whole blood.

A twenty-fourth aspect is the method of any of the eighteenth aspect through the twenty-third aspect further comprising administering an active agent to the subject.

While embodiments of the present disclosure have been shown and described, modifications thereof can be made by one skilled in the art without departing from the spirit and teachings of the disclosure. The embodiments described herein are exemplary only, and are not intended to be limiting. Many variations and modifications of the disclosure are possible and are within the scope of the disclosure. Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc. Moreover, as features of the present disclosure have been described independently, said features may be combined in manners as would be understood by one of ordinary skill in the art.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The discussion of a reference in the Background is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural or other details supplementary to those set forth herein.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed above and throughout the text are provided solely for their disclosure prior to the filing date of the present application. Nothing herein is to be construed as an admission that the inventors are not entitled to antedate such disclosure by virtue of prior disclosure.

Unless indicated otherwise, when a range of any type is disclosed or claimed it is intended to disclose or claim individually each possible number that such a range could reasonably encompass, including any sub-ranges encompassed therein. When describing a range of measurements every possible number that such a range could reasonably encompass can, for example, refer to values within the range with one significant digit more than is present in the end points of a range. Moreover, when a range of values is disclosed or claimed, which Applicant intends to reflect individually each possible number that such a range could reasonably encompass, Applicant also intends for the disclosure of a range to reflect, and be interchangeable with, disclosing any and all sub-ranges and combinations of sub-ranges encompassed therein. Accordingly, Applicant reserves the right to proviso out or exclude any individual members of any such group, including any sub-ranges or combinations of sub-ranges within the group, if for any reason Applicant chooses to claim less than the full measure of the disclosure.

What is claimed is:

1. A device for use during extracorporeal treatment of preeclampsia comprising:
   a first component comprising a bimodal synthetic carbon particle mixture and a first portion of whole blood, wherein the bimodal synthetic carbon particle mixture is present in the device prior to the extracorporeal treatment and wherein the first portion of whole blood is not present in the device prior to the extracorporeal treatment, and wherein a synthetic carbon particle of the bimodal synthetic carbon particle mixture is functionalized with one or more antibodies, anti-antibodies, anti-cytokines, synthetic ligands, or combinations thereof to enhance the affinity of the synthetic carbon particle for molecules to be removed from the first portion of whole blood;
   a second component comprising a first resin bead covalently functionalized with at least one affinity ligand directed toward syncytiotrophoblast-derived factor sEndoglin and a second portion of whole blood, wherein the least one affinity ligand directed toward syncytiotrophoblast-derived factor sEndoglin is covalently bonded to the first resin bead, wherein the first resin bead is present in the device prior to the extracorporeal treatment and wherein the second portion of whole blood is not present in the device prior to the extracorporeal treatment; and a third component comprising a second resin bead functionalized with at least one affinity ligand directed toward syncytiotrophoblast-derived factor soluble Fms-like tyrosine kinase-1 and a third portion of whole blood, wherein the least one affinity ligand directed toward syncytiotrophoblast-derived factor soluble Fms-like tyrosine kinase-1 is covalently bonded to the second resin bead, wherein the device comprises at least one column and the first component, the second component, and the third component are each disposed in one or more columns, wherein the second resin bead is present in the device prior to the extracorporeal treatment and wherein the third portion of whole blood is not present in the device prior to the extracorporeal treatment, wherein the device is configured to treat preeclampsia when the first and second resin beads have a particle size of from about 1 mm to about 12 mm, and wherein the first resin bead, the second resin bead, or both the first resin bead and the second resin bead comprises gelatin, collagen type I, fibrin glue, polyglycerol sebacate (PGS), polyglycolic acid (PGA), poly-1-lactide (PLA), poly(lactide-co-glycolide) (PLGA), polyvinyl alcohol (PVA), polycaprolactone, poly(N-isopropylacrylamide), sepharose, polyoxymethylene (POM), polyvinylchloride (PVC), polyvinylidene chloride (PVDC), polystyrene (PS), polyacrylate, polyacrylamide, polyglycidyl methacrylate (PGMA), acrylonitrile butadiene styrene (ABS), polyacrylonitrile (PAN), polyester, polycarbonate, polyethylene terephthalate (PET), polyamide, polyaramide, polyethylene glycol (PEG), polyvinylpyrrolidone (PVP), polysulfone (PS), polyethersulfone (PES), polyarylethersulfone (PEAS), ethylene vinyl acetate (EVA), ethylene vinyl alcohol (EVOH), polyamide-imide, polyaryletherketone (PAEK), polybutadiene (PBD), polybutylene (PB), polybutylene terephthalate (PBT), polyhydroxyalkanoate, polyether ether ketone (PEEK), polyether ketone ketone (PEKK), polyether imide (PEI), polyimide, polylactic acid (PLA), polymethyl pentene (PMP), poly(p-phenylene ether) (PPE), styrene acrylonitrile (SAN), polybutenoic acid, poly(4-allyl-benzoic acid), poly(glycidyl acrylate), polyglycidyl methacrylate (PGMA), poly(allyl glycidyl ether), poly(vinyl glycidyl ether), poly(vinyl glycidyl urethane), polyallylamine, polyvinylamine, copolymers of said polymers; derivatives of said polymers, or combinations thereof.

2. The device of claim 1, wherein the components are separated with at least one component in a second column.

3. The device of claim 1 wherein the bimodal synthetic carbon particle mixture comprises a first carbon particle having pore size x and a second carbon particle having pore size y where y is greater than x.

4. The device of claim 3, wherein y is two times x.

5. The device of claim 1, wherein the first resin bead, the second resin bead, or both the first resin bead and the second resin bead comprises polyvinyl alcohol.

6. The device of claim 1, further comprising a compatibilizer.

7. The device of claim 1, wherein the first resin bead is negatively charged.

8. The device of claim 1, wherein the second resin bead is positively charged.

* * * * *